United States Patent
Anglada et al.

(10) Patent No.: US 7,947,688 B2
(45) Date of Patent: May 24, 2011

(54) N-[3-(3-SUBSTITUTED-PYRAZOLO[1,5-A]PYRIMIDIN-7-YL)PHENYL]-SULFONAMIDES, AND COMPOSITIONS, AND METHODS RELATED THERETO

(75) Inventors: Luis Anglada, Barcelona (ES); Albert Palomer, Barcelona (ES); Marta Princep, Barcelona (ES); Antonio Guglietta, Molins de Rei (ES)

(73) Assignee: Ferrer Internacional, S.A., Barcelona (ES)

( * ) Notice: Subject to any disclaimer, the term of this patent is extended or adjusted under 35 U.S.C. 154(b) by 904 days.

(21) Appl. No.: 10/562,559

(22) PCT Filed: Jul. 22, 2004

(86) PCT No.: PCT/EP2004/008208
§ 371 (c)(1),
(2), (4) Date: May 30, 2006

(87) PCT Pub. No.: WO2005/014597
PCT Pub. Date: Feb. 17, 2005

(65) Prior Publication Data
US 2006/0270690 A1 Nov. 30, 2006

(30) Foreign Application Priority Data

Jul. 24, 2003 (ES) .................................. 200301746
Jul. 12, 2004 (ES) .................................. 200401697

(51) Int. Cl.
*A61P 21/02* (2006.01)
*A61P 25/08* (2006.01)
*C07D 487/04* (2006.01)
*A61K 31/519* (2006.01)
*C07D 279/02* (2006.01)
*C07D 267/04* (2006.01)
*A61K 31/541* (2006.01)
*A61K 31/554* (2006.01)

(52) U.S. Cl. ............. 514/259.3; 514/222.2; 514/211.01; 544/3; 540/544

(58) Field of Classification Search .................. 544/281, 544/3; 540/544; 514/259.31, 222.2, 211.01, 514/259.3
See application file for complete search history.

(56) References Cited

U.S. PATENT DOCUMENTS

| 4,626,538 A | 12/1986 | Dusza et al. |
| 4,654,347 A * | 3/1987 | Dusza et al. ................ 514/259.3 |
| 6,399,621 B1 | 6/2002 | Dusza et al. |

FOREIGN PATENT DOCUMENTS

| EP | 0 129 847 B1 | 1/1985 |
| EP | 0129847 | * 1/1985 |

OTHER PUBLICATIONS

Hanns Mohler et al.; Neurosciences, pp. 22-25, 2001.
David J. Nutt et al.; British Journal of Psychiatry, vol. 179, pp. 390-396, 2001.
H. Mohler et al.; The Journal of Pharmacology and Experimental Therapeutics; vol. 300, No. 1, pp. 2-8, 2002.
Uwe Rudolph et al.; Nature, vol. 401, pp. 796-800, Oct. 21, 1999.
George, C F P, Lancet, XX, XX, vol. 357, No. 9293, Nov. 10, 2001, pp. 1623-1626.

* cited by examiner

*Primary Examiner* — Susanna Moore
(74) *Attorney, Agent, or Firm* — Birch, Stewart, Kolasch & Birch, LLP

(57) ABSTRACT

The present invention relates to compounds of Formula (I): wherein $R_1$, $R_2$ and $R_3$ are as defined in the claims. The compounds have specific affinity for the $GABA_A$ receptor and are therefore useful in the treatment and prevention of diseases modulated by the $\alpha_1$- and $\alpha_2$-$GABA_A$ receptors.

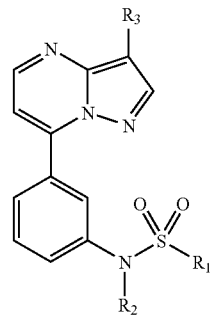

(I)

32 Claims, No Drawings

N-[3-(3-SUBSTITUTED-PYRAZOLO[1,5-A]PYRIMIDIN-7-YL)PHENYL]-SULFONAMIDES, AND COMPOSITIONS, AND METHODS RELATED THERETO

TECHNICAL FIELD

This invention is directed to agents with affinity for $GABA_A$ receptor, more specifically to pyrazolo[1,5-a]pyrimidines.

BACKGROUND OF THE INVENTION $GABA_A$ receptor (7-aminobutyric acid$_A$) is a pentameric protein which forms a membrane ion channel. $GABA_A$ receptor is implicated in the regulation of sedation, anxiety, muscle tone, epileptogenic activity and memory functions. These actions are due to defined subunits of $GABA_A$ receptor, particularly the $\alpha_1$- and $\alpha_2$-subunits.

Sedation is modulated by the $\alpha_1$-subunit. Zolpidem is characterized by a high affinity for the $\alpha_1$-receptors and its sedative and hypnotic action is mediated by these receptors in vivo. Similarly, the hypnotic action of zaleplon is also mediated by the $\alpha_1$-receptors.

The anxiolytic action of diazepam is mediated by the enhancement of GABAergic transmission in a population of neurons expressing the $\alpha_2$-receptors. This indicates that the $\alpha_2$-receptors are highly specific targets for the treatment of anxiety.

Muscle relaxation in diazepam is mainly mediated by $\alpha_2$-receptors, since these receptors exhibit a highly specific expression in spinal cord.

The anticonvulsant effect of diazepam is partly due to $\alpha_1$-receptors. In diazepam, a memory-impairing compound, anterograde amnesia is mediated by $\alpha_1$-receptors.

$GABA_A$ receptor and its $\alpha_1$- and $\alpha_2$-subunits have been widely reviewed by H. Möhler et al. (J. Pharmacol. Exp. Ther., 300, 2-8, 2002); H. Möhler et al. (Curr. Opin. Pharmacol., 1, 22-25, 2001); U. Rudolph et al. (Nature, 401, 796-800, 1999); and D. J. Nutt et al. (Br. J. Psychiatry, 179, 390-396, 2001).

Diazepam and other classical benzodiazepines are extensively used as anxiolytic agents, hypnotic agents, anticonvulsants and muscle relaxants. Their side effects include anterograde amnesia, decrease in motor activity and potentiation of ethanol effects.

In this context, the compounds of this invention are ligands of $\alpha_1$- and $\alpha_2$-$GABA_A$ receptor for their clinical application in sleep disorders, preferably insomnia, anxiety and epilepsy.

Insomnia is a highly prevalent disease. Its chronicity affects 10% of the population and 30% when transitory insomnia is computed as well. Insomnia describes the trouble in getting to sleep or staying asleep and is associated with next-day hangover effects such as weariness, lack of energy, low concentration and irritability. The social and health impact of this complaint is important and results in evident socioeconomic repercussions.

Pharmacological therapy in the management of insomnia firstly included barbiturates and chloral hydrate, but these drugs elicit numerous known adverse effects, for example, overdose toxicity, metabolic induction, and enhanced dependence and tolerance. In addition, they affect the architecture of sleep by decreasing above all the duration and the number of REM sleep stages. Later, benzodiazepines meant an important therapeutic advance because of their lower toxicity, but they still showed serious problems of dependence, muscle relaxation, amnesia and rebound insomnia following discontinuation of medication.

The latest known therapeutic approach has been the introduction of non-benzodiazepine hypnotics, such as pyrrolo[3,4-b]pyrazines (zopiclone), imidazo[1,2-a]pyridines (zolpidem) and, finally, pyrazolo[1,5-a]pyrimidines (zaleplon). Later, two new pyrazolo[1,5-a]pyrimidines, indiplon and ocinaplon, have entered into development, the latter with rather anxiolytic action. All these compounds show a rapid sleep induction and have less next-day hangover effects, lower potential for abuse and lower risk of rebound insomnia than benzodiazepines. The mechanism of action of these compounds is the alosteric activation of $GABA_A$ receptor through its binding to benzodiazepine binding site (C. F. P. George, The Lancet, 358, 1623-1626, 2001). While benzodiazepines are unspecific ligands at $GABA_A$ receptor binding site, zolpidem and zaleplon show a greater selectivity for $\alpha_1$-subunit. Notwithstanding that, these drugs still affect the architecture of sleep and may induce dependence in longterm treatments.

In U.S. Pat. No. 4,626,538 (zaleplon), U.S. Pat. Nos. 4,654,347, 6,399,621 (indiplon) and European Patent No. 129,847 (ocinaplon) hypnotic pyrazolo[1,5-a]pyrimidines are disclosed.

Research for new active compounds in the management of insomnia answers an underlying health need, because even recently introduced hypnotics still affect the architecture of sleep and may induce dependence in long-term treatments.

It is therefore desirable to focus on the development of new hypnotic agents with a lower risk of side effects.

Thus, the present invention is directed to new N-[3-(3-substituted-pyrazolo[1,5-a]pyrimidin-7-yl)-phenyl]-sulfonamides which are active versus $GABA_A$ and, particularly, versus its $\alpha_1$- and $\alpha_2$-subunits. Consequently, the compounds of this invention are useful in the treatment and prevention of all those diseases mediated by $GABA_A$ receptor $\alpha_1$- and $\alpha_2$-subunits. Non-limitative examples of such diseases are sleep disorders, preferably insomnia, anxiety and epilepsy. Non-limitative examples of the relevant indications of the compounds of this invention are all those diseases or conditions, such as insomnia or anesthesia, in which an induction of sleep, an induction of sedation or an induction of muscle relaxation are needed.

DETAILED DESCRIPTION OF THE INVENTION

The present invention relates to novel N-[3(3-substituted-pyrazolo[1,5-a]pyrimidin-7-yl)-phenyl]-sulfonamides of formula (I)

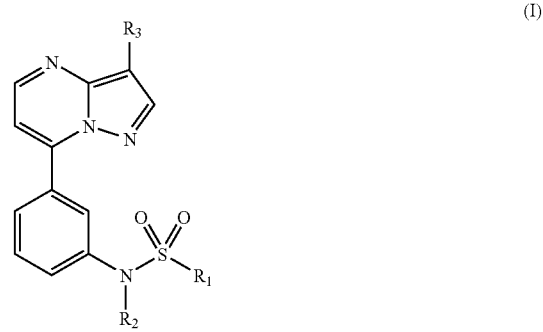

and their pharmaceutically acceptable salts;
wherein
$R_1$ is selected from the group consisting of alkyl($C_1$-$C_6$), alkenyl($C_2$-$C_6$), ω,ω,ω-trifluoroalkyl($C_1$-$C_6$), cycloalkyl($C_3$-$C_6$), cycloalkyl($C_3$-$C_6$)alkyl($C_1$-$C_6$), —O-alkyl($C_1$-$C_6$), —NH-alkyl($C_1$-$C_6$), —N(dialkyl($C_1$-$C_6$)), alkyl($C_1$-$C_6$)—O-alkyl($C_1$-$C_6$), alkyl($C_1$-$C_6$)—NH-alkyl($C_1$-$C_6$), alkyl($C_1$-$C_6$)—N(dialkyl($C_1$-$C_6$)), phenyl, monosubstituted phenyl, disubstituted phenyl, phenylalkyl($C_1$-$C_6$), phenylalkenyl($C_2$-$C_6$), furyl, substituted furyl, isoxazolyl, substituted isoxazolyl, pyrazolyl, substituted pyrazolyl, thienyl, substituted thienyl, thiazolyl, substituted thiazolyl, pyridyl and substituted pyridyl;

$R_2$ is selected from the group consisting of hydrogen, alkyl ($C_1$-$C_6$), alkenyl($C_2$-$C_6$), alkynyl($C_2$-$C_6$) and cycloalkyl($C_3$-$C_6$);

or else $R_1$ and $R_2$ form a cycle having the structure:

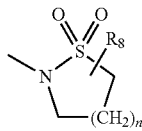

wherein n is an integer 1, 2 or 3 inclusive;

$R_3$ is selected from the group consisting of hydrogen, halogen, alkyl($C_1$-$C_6$), cycloalkyl($C_3$-$C_6$), alkenyl($C_2$-$C_6$), alkynyl($C_2$-$C_6$), —O-alkyl($C_1$-$C_6$), halo-alkyl($C_1$-$C_6$), —CN, —$SO_2$—$R_4$, —NH—$R_4$, —$COR_6$, —CO—$NHR_6$, —$COOR_6$, —C($NR_7$)$R_6$, phenyl, substituted phenyl, heteroaryl and substituted heteroaryl;

$R_4$ and $R_5$ are independently selected from the group consisting of alkyl($C_1$-$C_6$), cycloalkyl($C_3$-$C_6$), aryl and heteroaryl;

$R_6$ is selected from the group consisting of hydrogen, alkyl ($C_1$-$C_6$), alkenyl($C_2$-$C_6$), alkynyl($C_2$-$C_6$), cycloalkyl($C_3$-$C_6$), phenyl, substituted phenyl, furyl, substituted furyl, thienyl, substituted thienyl, thiazolyl, substituted thiazolyl, pyridyl and substituted pyridyl;

$R_7$ is selected from the group consisting of alkyl($C_1$-$C_6$), cycloalkyl($C_3$-$C_6$), —OH, —O-alkyl($C_1$-$C_6$), alkyl($C_1$-$C_6$)—O-alkyl($C_1$-$C_6$), alkyl($C_1$-$C_6$)—NH-alkyl($C_1$-$C_6$), alkyl($C_1$-$C_6$)—N(dialkyl($C_1$-$C_6$)), phenyl, monosubstituted phenyl, furyl, thienyl, thiazolyl and pyridyl; and $R_8$ is selected from the group consisting of hydrogen, alkyl ($C_1$-$C_6$), cycloalkyl($C_3$-$C_6$), aryl and substituted or unsubstituted heteroaryl;

with the proviso that:

$R_1$ may simultaneously not be p-tolyl and $R_2$ methyl and $R_3$ benzoyl; and $R_1$ may simultaneously not be p-tolyl and $R_2$ ethyl and $R_3$ furyl-2-carbonyl.

U.S. Pat. No. 4,654,347 (Example 80) discloses N-[3-(3-benzoyl-pyrazolo[1,5-a]pyrimidin-7-yl)phenyl]-N,4-dimethyl-benzenesulfonamide and European Patent No. 129.847 (Example 166) discloses N-ethyl-N-[3-[3-(2-furylcarbonyl)-pyrazolo[1,5-a]pyrimidin-7-yl]phenyl]-4-methyl-benzene-sulfonamide. These compounds are merely recited in the above patents as synthetic intermediates, and they are not considered pharmacologically active substances. This fact, therefore, does not suggest that analog compounds, like those in the instant invention, may be therapeutically interesting, which finding has unexpectedly been discovered by the applicants. These compounds, which are comprised in the general formula (I), have purposely been thus excluded from the scope of this invention.

$R_1$ is preferably selected from alkyl($C_1$-$C_6$); ω,ω,ω-trifluoroalkyl($C_1$-$C_6$); phenyl; phenyl substituted with 1 or 2 groups which are independently selected from halogen (in particular fluoro and chloro), cyano, $NO_2$, Oalkyl($C_1$-$C_6$) and alkyl($C_1$-$C_6$); phenylalkenyl($C_2$-$C_6$); cycloalkyl($C_3$-$C_6$); cycloalkyl ($C_3$-$C_6$)alkyl($C_1$-$C_6$); phenylalkyl($C_1$-$C_6$); alkenyl($C_2$-$C_6$); isoxazolyl which may be substituted with 1 or 2 alkyl($C_1$-$C_6$); furyl which may be substituted with 1 or 2 alkyl($C_1$-$C_6$); furyl which may be substituted with 1 alkyl($C_1$-$C_6$) and 1 trifluoromethyl; thiazolyl which may substituted with 1 or 2 alkyl ($C_1$-$C_6$); pyrazolyl which may be substituted with 1, 2 or 3 alkyl($C_1$-$C_6$); thienyl which may be substituted with 1 or 2 alkyl($C_1$-$C_6$) and pyridyl which may be substituted with 1 or 2 4-morpholinyl groups; or $R_1$ and $R_2$ together form the above mentioned cycle wherein n and $R_8$ are as defined above.

$R_2$ is preferably selected from H, alkyl($C_1$-$C_6$), cycloalkyl ($C_3$-$C_6$) and alkenyl($C_2$-$C_6$), or $R_2$ forms together with $R_1$ the above mentioned cycle wherein n and $R_8$ are as defined above.

$R_3$ is preferably selected from H, CN and $COR_6$ wherein $R_6$ is selected from phenyl which may be substituted with 1 or 2 groups which are independently selected from halogen (in particular fluoro or chloro), alkyl($C_1$-$C_6$) and Oalkyl($C_1$-$C_6$); thienyl; pyridyl and oxadiazolyl which may be substituted with alkyl($C_1$-$C_6$).

A preferred embodiment relates to the compounds of formula I wherein $R_3$ is cyano, $R_1$ is selected from alkyl($C_1$-$C_6$), phenyl and phenyl substituted with an Oalkyl($C_1$-$C_6$) group, and $R_2$ is selected from alkyl($C_1$-$C_6$), cycloalkyl($C_3$-$C_6$) and alkynyl($C_2$-$C_6$).

A further preferred embodiment relates to compounds of formula I, wherein $R_3$ is thiophene carbonyl, in particular thiophene-2-carbonyl, $R_1$ is selected from alkyl($C_1$-$C_6$); phenylalkenyl($C_2$-$C_6$); ω,ω,ω-trifluoroalkyl($C_1$-$C_6$); phenyl; phenyl substituted with 1 or 2 groups which are independently selected from halogen (in particular fluoro and chloro), cyano, Oalkyl($C_1$-$C_6$) and nitro; phenylalkyl($C_1$-$C_6$); cycloalkyl($C_3$-$C_6$); alkenyl($C_2$-$C_6$); cycloalkyl($C_3$-$C_6$)alkyl ($C_1$-$C_6$); isoxazolyl substituted with 1 or 2 alkyl ($C_1$-$C_6$); furyl substituted with 1 or 2 groups independently selected from alkyl($C_1$-$C_6$) and w,w,w-trifluoroalkyl($C_1$-$C_6$); thiazolyl substituted with 1 or 2 alkyl($C_1$-$C_6$); pyridyl which is substituted with a 4-morpholinyl group; thienyl; and pyrazolyl substituted with 1, 2 or 3 alkyl($C_1$-$C_6$), and $R_2$ is selected from H, alkyl($C_1$-$C_6$), cycloalkyl($C_3$-$C_6$) and alkynyl($C_2$-$C_6$).

A further preferred embodiment relates to compounds of formula I, wherein $R_3$ is selected from benzoyl, wherein the phenyl group may be substituted with halogen (in particular fluoro or chloro), alkyl($C_1$-$C_6$) and Oalkyl($C_1$-$C_6$); oxadiazolyl which is substituted with alkyl($C_1$-$C_6$) and pyridylcarbonyl; $R_1$ is alkyl($C_1$-$C_6$) and $R_2$ is H, alkyl($C_1$-$C_6$) or alkynyl ($C_2$-$C_6$).

Preferably, the present invention relates to new N-[3-(3-substituted-pyrazolo[1,5-a]pyrimidin-7-yl)-phenyl]-sulfonamides of formula (I) wherein $R_1$ is selected from the group consisting of methyl, ethyl, n-propyl, i-propyl, n-butyl, 2-phenylethenyl, 2,2,2-trifluoroethyl, phenyl, 2-chlorophenyl, 3-chlorophenyl, 4-chlorophenyl, 2,4-dichlorophenyl, 3,4-dichlorophenyl, 2-cyanophenyl, 3-cyanophenyl, 4-cyanophenyl, 4-methoxyphenyl, 3-nitrophenyl, 4-nitrophenyl, 2-thienyl, 5-methyl-4-isoxazolyl, 5-methyl-2-trifluoromethyl-3-furyl, 4-(4-morpholinyl)-3-pyridyl, 2,4-dimethyl-5-thiazolyl, cyclopropyl, benzyl, vinyl, 3,5-dimethyl-4-isoxazolyl, 1,3,5-trimethyl-4-pyrazolyl and cyclopentylmethyl; $R_2$ is selected from the group consisting of hydrogen, methyl, ethyl, n-propyl, i-propyl, n-butyl, cyclopropyl and 2-propynyl, or $R_1$ and $R_2$ form in conjunction with the —N—$SO_2$— group an isothiazolidine-1,1-dioxide ring, in such a way that $R_1$ and $R_2$ form together a 1,3-propylene group, and $R_3$ is selected from a cyano group, a benzoyl group, a 4-fluorobenzoyl group, a 4-methylbenzoyl group, a 4-methoxybenzoyl group, a 5-methyl-1,2,4-oxadiazol-3-yl group, a pyridyl-2-carbonyl group, a pyridyl-4-carbonyl group and a thiophene-2-carbonyl group.

"Heteroaryl" means 5- or 6-membered aromatic heterocyclic groups containing 1, 2 or 3 heteroatoms which are independently from each other selected from N, O and S. Examples for heteroaryl groups are pyridyl, pyrimidinyl, triazinyl, pyrrolyl, thienyl, furyl, oxazolyl, thiazolyl, imidazolyl, oxadiazolyl.

"Aryl" means preferably phenyl or naphthyl.

"Halogen" or "halo" means F, Cl, Br or I, preferably F or Cl.

"Cycloalkyl($C_3$-$C_6$)" preferably means cyclopropyl, cyclopentyl or cyclohexyl.

"Substituted" (including mono- and di-substituted) means that the group in question carries 1, 2 or 3 substituents which are independently from each other selected from alkyl($C_1$-$C_6$), Oalkyl($C_1$-$C_6$), halogen, CN and $NO_2$. In case of heteroaryl groups the substituent may also be attached to a hetero nitrogen atom.

Alkyl groups (also in —Oalkyl, —NHalkyl etc.) include straight chain and branched groups and preferably have 1 to 4 carbon atoms.

The term "pharmaceutically acceptable salt" used herein encompasses any salt formed from organic and inorganic acids, such as hydrobromic, hydrochloric, phosphoric, nitric, sulfuric, acetic, adipic, aspartic, benzenesulfonic, benzoic, citric, ethanesulfonic, formic, fumaric, glutamic, lactic, maleic, malic, malonic, mandelic, methanesulfonic, 1,5-naphthalendisulfonic, oxalic, pivalic, propionic, p-toluenesulfonic, succinic, tartaric acids and the like.

The preferred compounds of the present invention are shown below:

N-[3-(3-cyano-pyrazolo[1,5-a]pyrimidin-7-yl)-phenyl]-N-methyl-methanesulfonamide;
N-[3-(3-cyano-pyrazolo[1,5-a]pyrimidin-7-yl)-phenyl]-N-ethyl-methanesulfonamide;
N-[3-(3-cyano-pyrazolo[1,5-a]pyrimidin-7-yl)-phenyl]-N-methyl-benzenesulfonamide;
N-[3-(3-cyano-pyrazolo[1,5-a]pyrimidin-7-yl)-phenyl]-N-ethyl-benzenesulfonamide;
N-methyl-N-{3-[3-(thiophene-2-carbonyl)-pyrazolo[1,5-a]pyrimidin-7-yl]-phenyl}-methanesulfonamide;
N-ethyl-N-{3-[3-(thiophene-2-carbonyl)-pyrazolo[1,5-a]pyrimidin-7-yl]-phenyl}-methanesulfonamide;
N-methyl-N-{3-[3-(thiophene-2-carbonyl)-pyrazolo[1,5-a]pyrimidin-7-yl]-phenyl}-benzenesulfonamide;
N-ethyl-N-{3-[3-(thiophene-2-carbonyl)-pyrazolo[1,5-a]pyrimidin-7-yl]-phenyl}-benzenesulfonamide;
N-2-propynyl-N-{3-[3-(thiophene-2-carbonyl)-pyrazolo[1,5-a]pyrimidin-7-yl]-phenyl}-methanesulfonamide;
N-propyl-N-{3-[3-(thiophene-2-carbonyl)-pyrazolo[1,5-a]pyrimidin-7-yl]-phenyl}-ethanesulfonamide;
N-ethyl-N-{3-[3-(thiophene-2-carbonyl)-pyrazolo[1,5-a]pyrimidin-7-yl]-phenyl}-ethanesulfonamide;
N-2-propynyl-N-{3-[3-(thiophene-2-carbonyl)-pyrazolo[1,5-a]pyrimidin-7-yl]-phenyl}-2-propanesulfonamide;
N-methyl-N-{3-[3-(thiophene-2-carbonyl)-pyrazolo[1,5-a]pyrimidin-7-yl]-phenyl}-ethanesulfonamide;
N-butyl-N-{3-[3-(thiophene-2-carbonyl)-pyrazolo[1,5-a]pyrimidin-7-yl]-phenyl}-ethanesulfonamide;
7-(3-(2-isothiazolidinyl-1,1-dioxide)-phenyl)-3-(thiophene-2-carbonyl)-pyrazolo[1,5-a]pyrimidine;
N-methyl-N-{3-[3-(thiophene-2-carbonyl)-pyrazolo[1,5-a]pyrimidin-7-yl]-phenyl}-2-propanesulfonamide;
N-ethyl-N-{3-[3-(thiophene-2-carbonyl)-pyrazolo[1,5-a]pyrimidin-7-yl]-phenyl}-2-propanesulfonamide;
N-propyl-N-{3-[3-(thiophene-2-carbonyl)-pyrazolo[1,5-a]pyrimidin-7-yl]-phenyl}-2-propanesulfonamide;
N-butyl-N-{3-[3-(thiophene-2-carbonyl)-pyrazolo[1,5-a]pyrimidin-7-yl]-phenyl}-2-propanesulfonamide;
N-[3-(3-cyano-pyrazolo[1,5-a]pyrimidin-7-yl)-phenyl]-N-2-propynyl-methanesulfonamide;
N-[3-(3-cyano-pyrazolo[1,5-a]pyrimidin-7-yl)-phenyl]-N-propyl-ethanesulfonamide;
N-[3-(3-cyano-pyrazolo[1,5-a]pyrimidin-7-yl)-phenyl]-N-ethyl-ethanesulfonamide;
N-[3-(3-cyano-pyrazolo[1,5-a]pyrimidin-7-yl)-phenyl]-N-2-propynyl-propane-2-sulfonamide;
N-[3-(3-cyano-pyrazolo[1,5-a]pyrimidin-7-yl)-phenyl]-N-methyl-ethanesulfonamide;
N-[3-(3-cyano-pyrazolo[1,5-a]pyrimidin-7-yl)-phenyl]-N-butyl-ethanesulfonamide;
7-(3-(2-isothiazolidinyl-1,1-dioxide)-phenyl)-3-cyano-pyrazolo[1,5-a]pyrimidine;
N-[3-(3-cyano-pyrazolo[1,5-a]pyrimidin-7-yl)-phenyl]-N-methyl-2-propanesulfonamide;
N-[3-(3-cyano-pyrazolo[1,5-a]pyrimidin-7-yl)-phenyl]-N-ethyl-2-propanesulfonamide;
N-[3-(3-cyano-pyrazolo[1,5-a]pyrimidin-7-yl)-phenyl]-N-butyl-2-propanesulfonamide;
N-[3-(3-cyano-pyrazolo[1,5-a]pyrimidin-7-yl)-phenyl]-N-propyl-2-propanesulfonamide;
N-[3-(3-cyano-pyrazolo[1,5-a]pyrimidin-7-yl)-phenyl]-N-2-propynyl-ethanesulfonamide;
N-methyl-N-{3-[3-(pyridin-2-carbonyl)-pyrazolo[1,5-a]pyrimidin-7-yl]-phenyl}-methanesulfonamide;
N-ethyl-N-{3-[3-(pyridin-2-carbonyl)-pyrazolo[1,5-a]pyrimidin-7-yl]-phenyl}-methanesulfonamide;
N-2-propynyl-N-{3-[3-(pyridin-2-carbonyl)-pyrazolo[1,5-a]pyrimidin-7-yl]-phenyl}-methanesulfonamide;
N-methyl-N-{3-[3-(pyridin-2-carbonyl)-pyrazolo[1,5-a]pyrimidin-7-yl]-phenyl}-ethanesulfonamide;
N-ethyl-N-{3-[3-(pyridin-2-carbonyl)-pyrazolo[1,5-a]pyrimidin-7-yl]-phenyl}-ethanesulfonamide;
N-2-propynyl-N-{3-[3-(pyridin-2-carbonyl)-pyrazolo[1,5-a]pyrimidin-7-yl]-phenyl}-ethanesulfonamide;
N-methyl-N-{3-[3-(pyridin-4-carbonyl)-pyrazolo[1,5-a]pyrimidin-7-yl]-phenyl}-methanesulfonamide;
N-ethyl-N-{3-[3-(pyridin-4-carbonyl)-pyrazolo[1,5-a]pyrimidin-7-yl]-phenyl}-methanesulfonamide;
N-methyl-N-{3-[3-(pyridin-4-carbonyl)-pyrazolo[1,5-a]pyrimidin-7-yl]-phenyl}-ethanesulfonamide;
N-ethyl-N-{3-[3-(pyridin-4-carbonyl)-pyrazolo[1,5-a]pyrimidin-7-yl]-phenyl}-ethanesulfonamide;
N-2-propynyl-N-{3-[3-(pyridin-4-carbonyl)-pyrazolo[1,5-a]pyrimidin-7-yl]-phenyl}-ethanesulfonamide;
N-2-propynyl-N-{3-[3-(pyridin-4-carbonyl)-pyrazolo[1,5-a]pyrimidin-7-yl]-phenyl}-methanesulfonamide;
N-methyl-N-{3-[3-(fluorobenzene-4-carbonyl)-pyrazolo[1,5-a]pyrimidin-7-yl]-phenyl}-methanesulfonamide;
N-ethyl-N-{3-[(3-fluorobenzene-4-carbonyl)-pyrazolo[1,5-a]pyrimidin-7-yl]-phenyl}-methanesulfonamide;
N-methyl-N-{3-[3-(fluorobenzene-4-carbonyl)-pyrazolo[1,5-a]pyrimidin-7-yl]-phenyl}-ethanesulfonamide;
N-ethyl-N-{3-[3-(fluorobenzene-4-carbonyl)-pyrazolo[1,5-a]pyrimidin-7-y]-phenyl}-ethanesulfonamide;
N-2-propynyl-N-{3-[3-(fluorobenzene-4-carbonyl)-pyrazolo[1,5-a]pyrimidin-7-yl]-phenyl}-ethanesulfonamide;
N-2-propynyl-N-{3-[3-(fluorobenzene-4-carbonyl)-pyrazolo[1,5-a]pyrimidin-7-yl]-phenyl}-methanesulfonamide;

N-methyl-N-{3-[3-(4-methoxybenzoyl)-pyrazolo[1,5-a]pyrimidin-7-yl]-phenyl}-methanesulfonamide;
N-ethyl-N-{3-[3-(4-methoxybenzoyl)-pyrazolo[1,5-a]pyrimidin-7-yl]-phenyl}-methanesulfonamide;
N-methyl-N-{3-[3-(4-methoxybenzoyl)-pyrazolo[1,5-a]pyrimidin-7-yl]-phenyl}-ethanesulfonamide;
N-ethyl-N-{3-[3-(4-methoxybenzoyl)-pyrazolo[1,5-a]pyrimidin-7-yl]-phenyl}-ethanesulfonamide;
N-2-propynyl-N-{3-[3-(4-methoxybenzoyl)-pyrazolo[1,5-a]pyrimidin-7-yl]-phenyl}-ethanesulfonamide;
N-2-propynyl-N-{3-[3-(4-methoxybenzoyl)-pyrazolo[1,5-a]pyrimidin-7-yl]-phenyl}-methanesulfonamide;
N-methyl-N-{3-[3-(4-methylbenzoyl)-pyrazolo[1,5-a]pyrimidin-7-yl]-phenyl}-methanesulfonamide;
N-ethyl-N-{3-[3-(4-methylbenzoyl)-pyrazolo[1,5-a]pyrimidin-7-yl]-phenyl}-methanesulfonamide;
N-methyl-N-{3-[3-(4-methylbenzoyl)-pyrazolo[1,5-a]pyrimidin-7-yl]-phenyl}-ethanesulfonamide;
N-ethyl-N-{3-[3-(4-methylbenzoyl)-pyrazolo[1,5-a]pyrimidin-7-yl]-phenyl}-ethanesulfonamide;
N-2-propynyl-N-{3-[3-(4-methylbenzoyl)-pyrazolo[1,5-a]pyrimidin-7-yl]-phenyl}-ethanesulfonamide;
N-2-propynyl-N-{3-[3-(4-methylbenzoyl)-pyrazolo[1,5-a]pyrimidin-7-yl]-phenyl}-methanesulfonamide;
N-methyl-N-{3-[3-(benzoyl)-pyrazolo[1,5-a]pyrimidin-7-yl]-phenyl}-methanesulfonamide;
N-ethyl-N-{3-[3-(benzoyl)-pyrazolo[1,5-a]pyrimidin-7-yl]-phenyl}-methanesulfonamide;
N-methyl-N-{3-[3-(benzoyl)-pyrazolo[1,5-a]pyrimidin-7-yl]-phenyl}-ethanesulfonamide;
N-ethyl-N-{3-[3-(benzoyl)-pyrazolo[1,5-a]pyrimidin-7-yl]-phenyl}-ethanesulfonamide;
N-2-propynyl-N-{3-[3-(benzoyl)-pyrazolo[1,5-a]pyrimidin-7-yl]-phenyl}-ethanesulfonamide;
N-2-propynyl-N-{3-[3-(benzoyl)-pyrazolo[1,5-a]pyrimidin-7-yl]-phenyl}-methanesulfonamide;
N-methyl-N-{3-[3-(thiophene-2-carbonyl)-pyrazolo[1,5-a]pyrimidin-7-yl]-phenyl}-2-phenylethenesulfonamide;
N-methyl-N-{3-[3-(thiophene-2-carbonyl)-pyrazolo[1,5-a]pyrimidin-7-yl]-phenyl}-2,2,2-trifluoroethane-sulfonamide;
N-methyl-N-{3-[3-(thiophene-2-carbonyl)-pyrazolo[1,5-a]pyrimidin-7-yl]-phenyl}-2-chlorobenzenesulfonamide;
N-methyl-N-{3-[3-(thiophene-2-carbonyl)-pyrazolo[1,5-a]pyrimidin-7-yl]-phenyl}-3-chlorobenzenesulfonamide;
N-methyl-N-{3-[3-(thiophene-2-carbonyl)-pyrazolo[1,5-a]pyrimidin-7-yl]-phenyl}-4-chlorobenzenesulfonamide;
N-methyl-N-{3-[3-(thiophene-2-carbonyl)-pyrazolo[1,5-a]pyrimidin-7-yl]-phenyl}-2,4-dichlorobenzene-sulfonamide;
N-methyl-N-{3-[3-(thiophene-2-carbonyl)-pyrazolo[1,5-a]pyrimidin-7-yl]-phenyl}-3,4-dichlorobenzene-sulfonamide;
N-methyl-N-{3-[3-(thiophene-2-carbonyl)-pyrazolo[1,5-a]pyrimidin-7-yl]-phenyl}-2-cyanobenzenesulfonamide;
N-methyl-N-{3-[3-(thiophene-2-carbonyl)-pyrazolo[1,5-a]pyrimidin-7-yl]-phenyl}-3-cyanobenzenesulfonamide;
N-methyl-N-{3-[3-(thiophene-2-carbonyl)-pyrazolo[1,5-a]pyrimidin-7-yl]-phenyl}-4-cyanobenzenesulfonamide;
N-methyl-N-{3-[3-(thiophene-2-carbonyl)-pyrazolo[1,5-a]pyrimidin-7-yl]-phenyl}-3-nitrobenzenesulfonamide;
N-methyl-N-{3-[3-(thiophene-2-carbonyl)-pyrazolo[1,5-a]pyrimidin-7-yl]-phenyl}-4-nitrobenzenesulfonamide;
N-methyl-N-{3-[3-(thiophene-2-carbonyl)-pyrazolo[1,5-a]pyrimidin-7-yl]-phenyl}-2-thiophenesulfonamide;
N-methyl-N-{3-[3-(thiophene-2-carbonyl)-pyrazolo[1,5-a]pyrimidin-7-yl]-phenyl}-5-methyl-4-isoxazolyl-sulfonamide;
N-methyl-N-{3-[3-(thiophene-2-carbonyl)-pyrazolo[1,5-a]pyrimidin-7-yl]-phenyl}-2-trifluoromethyl-5-methyl-3-furylsulfonamide;
N-methyl-N-{3-[3-(thiophene-2-carbonyl)-pyrazolo[1,5-a]pyrimidin-7-yl]-phenyl}-6-(morpholin-4-yl)-3-pyridylsulfonamide;
N-methyl-N-{3-[(3-(thiophene-2-carbonyl)-pyrazolo[1,5-a]pyrimidin-7-yl]-phenyl}-2,4-dimethyl-5-thiazolyl-sulfonamide;
N-methyl-N-{3-[3-(thiophene-2-carbonyl)-pyrazolo[1,5-a]pyrimidin-7-yl]-phenyl}-cyclopropylsulfonamide;
N-methyl-N-{3-[3-(thiophene-2-carbonyl)-pyrazolo[1,5-a]pyrimidin-7-yl]-phenyl}-benzylsulfonamide;
N-methyl-N-{3-[3-(thiophene-2-carbonyl)-pyrazolo[1,5-a]pyrimidin-7-yl]-phenyl}-vinylsulfonamide;
N-methyl-N-{3-[3-(thiophene-2-carbonyl)-pyrazolo[1,5-a]pyrimidin-7-yl]-phenyl}-3,5-dimethyl-4-isoxazolyl-sulfonamide;
N-methyl-N-{3-[3-(thiophene-2-carbonyl)-pyrazolo[1,5-a]pyrimidin-7-yl]-phenyl}-1,3,5-trimethyl-4-pyrazolyl-sulfonamide;
N-methyl-N-{3-[3-(thiophene-2-carbonyl)-pyrazolo[1,5-a]pyrimidin-7-yl]-phenyl}-propanesulfonamide;
N-methyl-N-{3-[(3-(thiophene-2-carbonyl)-pyrazolo[1,5-a]pyrimidin-7-yl]-phenyl}-butanesulfonamide;
N-methyl-N-{3-[3-(thiophene-2-carbonyl)-pyrazolo[1,5-a]pyrimidin-7-yl]-phenyl}-cyclopentylmethane-sulfonamide;
N-{3-[3-(5-methyl-[1,2,4]oxadiazol-3-yl)-pyrazolo[1,5-a]pyrimidin-7-yl]-phenyl}-methanesulfonamide; and
N-ethyl-N-{3-[3-(5-methyl-[1,2,4]oxadiazol-3-yl)-pyrazolo[1,5-a]pyrimidin-7-yl]-phenyl}-methanesulfonamide.

Another embodiment of the present invention is to provide a process for preparing the compounds of formula (I) and their pharmaceutically acceptable salts.

Another embodiment of the present invention is to provide a method for treating or preventing diseases associated with $GABA_A$ receptor modulation in a mammal which comprises administering to said mammal an effective amount of a compound of formula (I) or a pharmaceutically acceptable salt thereof.

Another embodiment of the present invention is to provide a method for treating or preventing diseases associated with $\alpha_1$-$GABA_A$ receptor modulation in a mammal which comprises administering to said mammal an effective amount of a compound of formula (I) or a pharmaceutically acceptable salt thereof.

Another embodiment of the present invention is to provide a method for treating or preventing diseases associated with $\alpha_2$-$GABA_A$ receptor modulation in a mammal which comprises administering to said mammal an effective amount of a compound of formula (I) or a pharmaceutically acceptable salt thereof.

Another embodiment of the present invention is to provide a method for treating or preventing anxiety in a mammal which comprises administering to said mammal an effective amount of a compound of formula (I) or a pharmaceutically acceptable salt thereof.

Another embodiment of the present invention is to provide a method for treating or preventing epilepsy in a mammal which comprises administering to said mammal an effective amount of a compound of formula (I) or a pharmaceutically acceptable salt thereof.

Another embodiment of the present invention is to provide a method for treating or preventing sleep disorders in a mammal which comprises administering to said mammal an effective amount of a compound of formula (I) or a pharmaceutically acceptable salt thereof.

Another embodiment of the present invention is to provide a method for treating or preventing insomnia in a mammal which comprises administering to said mammal an effective amount of a compound of formula (I) or a pharmaceutically acceptable salt thereof.

Another embodiment of the present invention is to provide a method for inducing sedation-hypnosis in a mammal which comprises administering to said mammal an effective amount of a compound of formula (I) or a pharmaceutically acceptable salt thereof.

Another embodiment of the present invention is to provide a method for inducing anesthesia in a mammal which comprises administering to said mammal an effective amount of a compound of formula (I) or a pharmaceutically acceptable salt thereof.

Another embodiment of the present invention is to provide a method for modulating the necessary time to induce sleep and its duration in a mammal which comprises administering to said mammal an effective amount of a compound of formula (I) or a pharmaceutically acceptable salt thereof.

Another embodiment of the present invention is to provide a method for inducing muscle relaxation in a mammal which comprises administering to said mammal an effective amount of a compound of formula (I) or a pharmaceutically acceptable salt thereof.

Another embodiment of the present invention is to provide a pharmaceutical composition containing a compound of formula (I) or a pharmaceutically acceptable salt thereof in association with therapeutically inert carriers.

The compositions include those suitable for oral, rectal and parenteral (including subcutaneous, intramuscular, and intravenous) administration, although the most suitable route will depend on the nature and severity of the condition being treated. The most preferred route of the present invention is the oral route. The compositions may be conveniently presented in unit dosage form, and prepared by any of the methods well known in the art of pharmacy.

The active compound can be combined with a pharmaceutical carrier according to conventional pharmaceutical compounding techniques. The carrier may take a wide variety of forms depending on the form of the preparation desired for administration, e.g. oral or parenteral (including intravenous injections or infusions). In preparing the compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, emulsions and elixirs); aerosols; or carriers such as starches, sugars, micro-crystalline cellulose, diluents, granulating agents, lubricants, binders, disintegrating agents and the like, in the case of oral solid preparations (such as for example, powders, capsules, and tablets) with the oral solid preparations being preferred over the oral liquid preparations.

Because of their ease of administration, tablets and capsules represent the most advantageous oral dosage unit form, in which case solid pharmaceutical carriers are employed. If desired, tablets may be coated by standard aqueous or non-aqueous techniques.

A suitable dosage range for use is from about 0.01 mg to about 100,00 mg total daily dose, given as a once daily administration or in divided doses if required.

The compounds of general formula (I) may be prepared according to the reaction shown in Scheme 1.

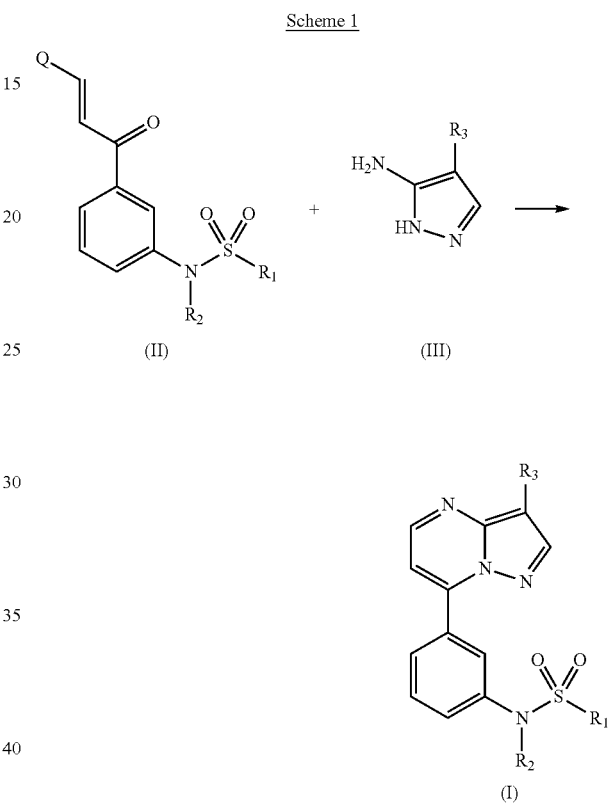

$R_1$, $R_2$ and $R_3$ are as described above and Q is an appropriate leaving group consisting of N(dialkyl($C_1$-$C_6$)), alkylthio ($C_1$-$C_6$) and alkoxy($C_1$-$C_6$). Preferably Q is selected from the group consisting of dimethylamino, methylthio or methoxy.

The reaction of aminopyrazole of general formula (III) with appropriately substituted 1-aryl-2-propen-1-one (II) is carried out in an inert polar protic or aprotic solvent such as glacial acetic acid, ethanol, methanol, dimethylformamide or dimethylsulfoxide at a temperature ranging from 50° to 130° C. After elapsing several hours (reaction time), the solvent is removed and the residue obtained is partitioned between an aqueous solution of sodium bicarbonate and dichloromethane. The crude resulting from evaporating the organic layer to dryness may be purified by one of the following methods: (a) silica gel chromatography using ethyl acetate or dichloromethane/methanol as eluent; or (b) crystallization in a suitable solvent (ethyl acetate, ethanol, methanol, etc.).

The intermediate of formula (II) when Q is dimethylamino [intermediate (VI)] can be obtained following the reaction sequence shown in Scheme 2

Scheme 2

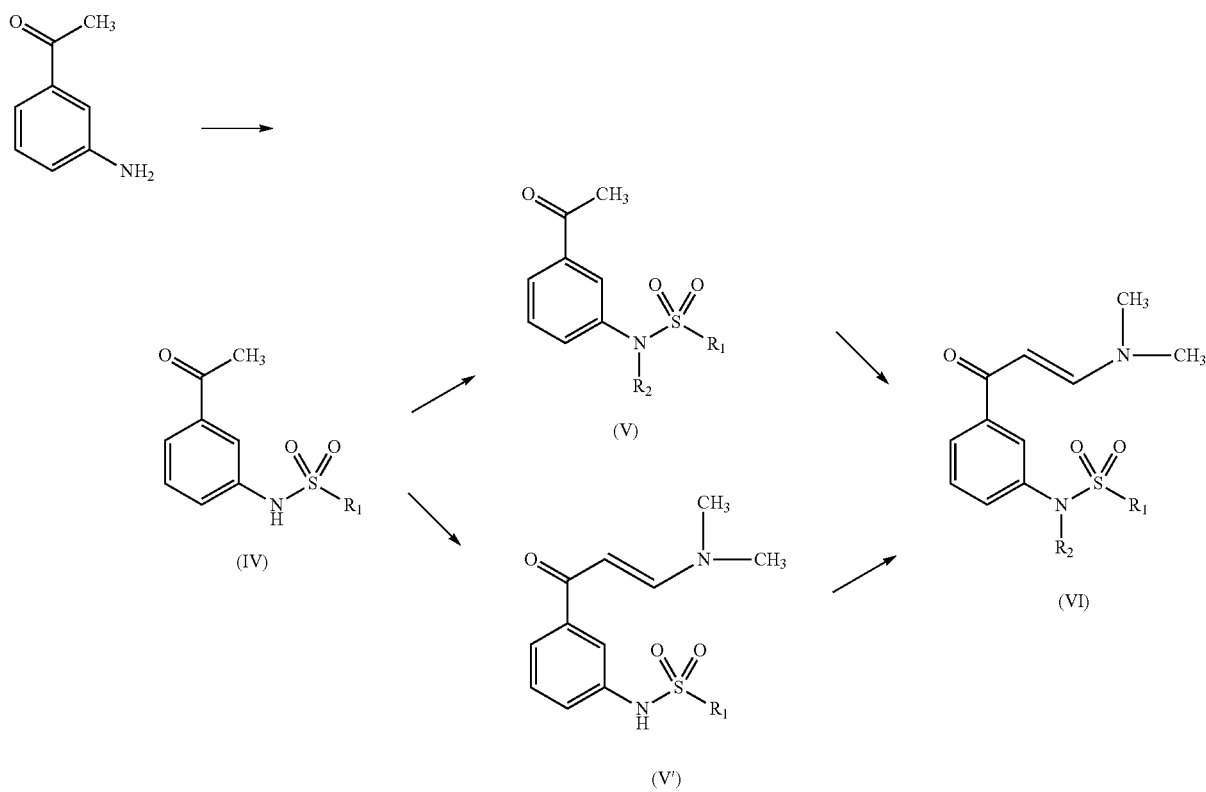

wherein R₁ and R₂ are as described above.

The sulfonamides of formula (IV) are prepared according to the method described by R. H. Uloth et al (J. Med. Chem. 9, 88-96, 1966).

The alkylation of the sulfonamides (IV) leading to the intermediates of formula (V) is performed, in accordance with methods well known by experts in Organic Chemistry, via formation of an anion and subsequent reaction with an alkyl halide.

The enaminones of formula (VI) are prepared according to general synthetic procedures of enamines described by J. M. Domagala et al (J. Heterocyclic Chem., 26(4), 1147-58, 1989); and K. Sawada et al (Chem. Pharm. Bull., 49(7), 799-813, 2001) by reacting an acetophenone with N,N-dimethylformamide dimethylacetal (DMFDMA) or Bredereck's reagent (tert-butoxybis(dimethylamino)methane).

The intermediates of formula (II), when Q is dimethylamino and R₂ is methyl (VII), can alternatively be prepared according to Scheme 3.

Scheme 3

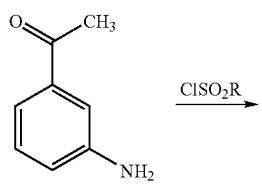

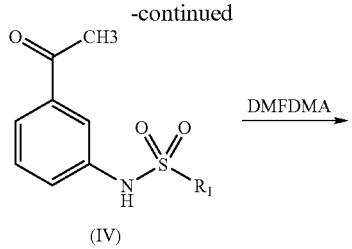

-continued

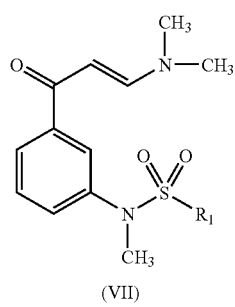

The conversion of (IV) into (VII) leads to the formation of the enaminone and, simultaneously, the formation of the N-methyl-sulfonamide as a result of the use of the properties of the N,N-dimethylformamide dimethyl acetal as a methylating agent.

Intermediate (VII) can also be prepared according to Scheme 4.

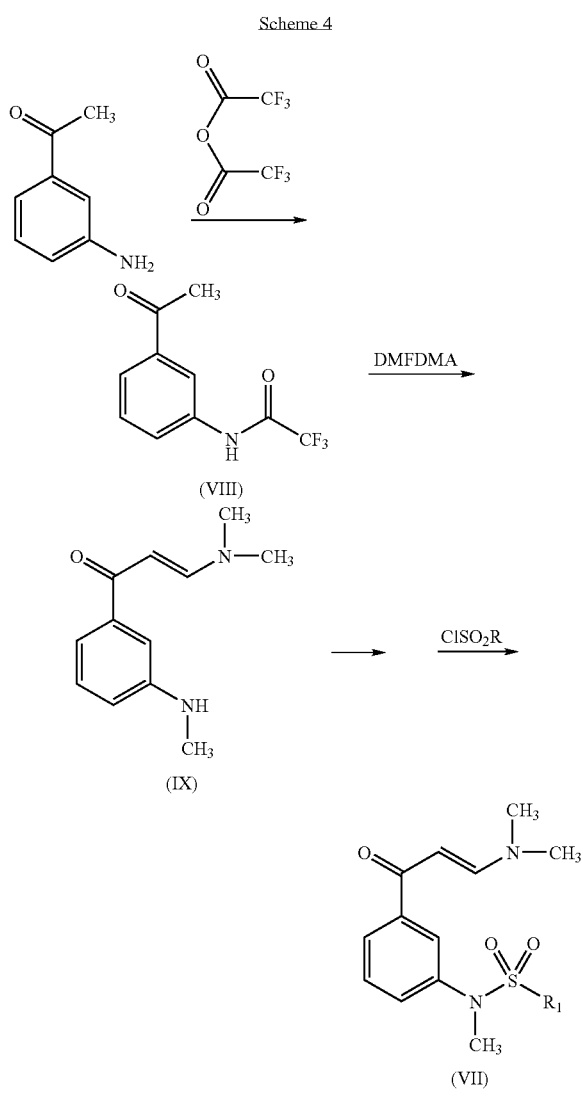

The advantage of this process is based on the fact that the formation of the sulfonamide takes place in the last stage of process. As a result, the total number of reaction steps is reduced in the preparation of large series of products. Moreover, as shown in the scheme, the conversion of (VIII) into (IX) leads to three following reactions in a one-pot process: (a) formation of the anaminone; (b) methylation of the trifluoroacetamide; and (c) deacylation yielding the N-methylated amine. The subsequent reaction of (IX) with the corresponding sulfonic acid chloride leads to obtaining intermediates (VII).

The preparation of intermediates (VII) by reaction between intermediates (IV) and N,N-dimethylformamide dimethyl acetal has not ever disclosed in the chemical literature and is another embodiment of the present invention.

Similarly, the preparation of intermediates (VII) by reaction between N-(3-acetylphenyl)-2,2,2-trifluoro-acetamide (VIII) and N,N-dimethylformamide dimethyl acetal, followed by the formation of the sulfonamide by reaction with the corresponding sulfonic acid chloride have not disclosed either in the chemical literature and is another embodiment of the present invention.

From the compounds of general formula (I) it is possible to obtain their pharmaceutically acceptable salts by treatment with the corresponding acids.

The applicants have discovered that the compounds of the present invention have a high affinity for $\alpha_1$- and $\alpha_2$-GABA$_A$ receptors as shown in Tables and 2. These in vitro results are consistent with those in vivo results obtained in sedation-hypnosis tests (Table 3).

In accordance with the results obtained, certain compounds of the present invention have surprisingly evidenced pharmacological activity both in vitro and in vivo, which has been similar to or higher than that of prior-art compounds. All these results support!their use in diseases or conditions modulated by $\alpha_1$- and $\alpha_2$-GABA$_A$ receptors, such as insomnia or anesthesia, in which an induction of sleep, an induction of sedation or an induction of muscle relaxation are needed.

The pharmacological activity of the compounds of the present invention has been determined as shown below.

Ligand-binding assays. Determination of the affinity of test compounds for $\alpha_1$- and $\alpha_2$-GABA$_A$ receptor.

Male Sprague-Dawley rats weighing 200-250 g at the time of experiment were used. After decapitation of the animal, the cerebellum (tissue that mostly contains $\alpha_1$-GABA$_A$ receptor) and spinal cord (tissue that mostly contains $\alpha_2$-GABA$_A$ receptor) were removed. The membranes were prepared according to the method by J. Lameh et al. (Prog. Neuro-Psychopharmacol. Biol. Psychiatry, 24, 979-991, 2000). Once the tissues weighed, they were suspended in 50 mM Tris.HCl (pH 7.7), 1:40 (v/v), homogenized and then centrifuged at 20000 g for 10 min at 7° C. The resulting pellet was resuspended under the same conditions and centrifuged again. The pellet was finally resuspended on a minimum volume and kept at −80° C. overnight. On the next day, the process was repeated until the final pellet was resuspended at a ratio of 1:10 (v/v).

Affinity was determined by competitive tests using radiolabeled flumazenil as ligand. The tests were performed according to the methods described by S. Arbilla et al. (Eur. J. Pharmacol., 130, 257-263, 1986); and Y. Wu et al. (Eur. J. Pharmacol., 278, 125-132, 1995). The membranes containing the study receptors, flumazenil (radiolabeling at a final concentration of 1 nM) and ascending concentrations of test compounds (in a total volume of 500 μl in 50 nM [ph 7.4] Tris.HCl buffer) were incubated. Simultaneously, the membranes were only incubated with the radiolabeled flumazenil (total binding, 100%) and in the presence of an elevated concentration of unradiolabeled flumazenil (non-specific binding, % estimation of radiolabeled ligand). The reactions started on adding the radiolabeled ligand followed by incubation for 60 minutes at 0° C. At the end of the incubation period, the tubes were filtered using a Brandel Mod. M-48R harvester and then washed three times with cold test buffer. The harvester was fitted with a GF/B filter that retained the membranes containing the receptors and the radiolabeled ligand which had been bound to the receptors. Then the filters were removed and left till dry. Once dried, the filters were cut, placed in vials with scintillation liquid and left under stirring overnight. The next day the filters were counted using a Packard Mod. Tricarb scintillation counter. For analysis of the results the percentage of specific binding for every concentration of test compound was calculated as follows:

% specific binding=$(X-N/T-N) \times 100$ where,

X: amount of bound ligand for every concentration of compound.

T: total binding, maximum amount bound to the radiolabeled ligand.

N: non-specific binding, amount of radiolabeled ligand bound in a non-specific way irrespective of the receptor used.

Every concentrations of compound were tested in duplicate and their mean values were used to determine the experimental values of % specific binding versus the concentration of compound. The values thus attained were fitted to a equation for competitive assays (SigmaPlot, SPSS Inc.) and the $IC_{50}$ values (concentration of compound able to inhibit by 50% the specific binding). Inhibition constants ($K_i$) were calculated from the $IC_{50}$ values according to Cheng-Prusoff's formula (Y. Cheng y W. H. Prusoff, Biochem. Pharmacol., 22(23), 3099-3108, 1973). The affinity data for subunit $\alpha_2$ are alternatively expressed as % inhibition at the concentrations of $10^{-5}$ M and $10^{-7}$ M. The results of these tests are given in Tables 1 and 2.

TABLE 1

Affinity for $\alpha_1$-GABA$_A$ receptor

| Compound | Ki (nM) |
| --- | --- |
| Example 2 | 74.5 |
| Example 3 | 7.4 |
| Example 5 | 13.4 |
| Example 6 | 3.0 |
| Example 16 | 0.7 |
| Example 17 | 28.0 |
| Example 18 | 5.9 |
| Example 19 | 0.5 |
| Example 20 | 12.5 |
| Example 22 | 20.9 |
| Example 23 | 26.7 |
| Example 24 | 30.7 |
| Example 25 | 26.6 |
| Example 27 | 28.2 |
| Example 29 | 53.2 |
| Example 30 | 52.1 |
| Example 33 | 608.7 |
| Example 34 | 33.2 |
| Example 35 | 88.9 |
| Example 37 | 577.8 |
| Example 38 | 119.4 |
| Example 39 | 37.2 |
| Example 40 | 7.3 |
| Example 46 | 41.0 |
| Example 51 | 38.7 |
| Example 52 | 48.1 |
| Example 53 | 33.2 |
| Example 58 | 47.9 |
| Example 63 | 62.1 |
| Example 64 | 32.9 |
| Example 68 | 8.9 |
| Example 69 | 16.6 |
| Example 70 | 6.2 |
| Example 72 | 14.6 |
| Example 76 | 201.2 |
| Example 77 | 35.6 |
| Example 78 | 2031.0 |
| Example 79 | 499.0 |
| Example 82 | 63.6 |
| Example 83 | 42.0 |
| Example 84 | 28.9 |
| Example 87 | 1.9 |
| Example 91 | 2.8 |
| Example 92 | 0.4 |
| Example 94 | 0.5 |
| Zaleplon | 198.9 |

TABLE 2

Affinity for $\alpha_2$-GABA$_A$ receptor

| Compound | $K_i$ (nM) | |
| --- | --- | --- |
| Example 2 | 831.3 | |
| Example 3 | 36.7 | |
| Example 5 | 290.2 | |
| Example 6 | 34.9 | |
| Zaleplon | 1302.5 | |
| Compound | % Inhibition ($10^{-5}$ M) | % Inhibition ($10^{-7}$ M) |
| Example 16 | 100.2 | 87.2 |
| Example 17 | 74.5 | 0 |
| Example 18 | 93.7 | 20.7 |
| Example 19 | 94.4 | 45.2 |
| Example 20 | 97.7 | 40.3 |
| Example 22 | 98.2 | 24.2 |
| Example 23 | 93.8 | 45.5 |
| Example 24 | 83.0 | 10.4 |
| Example 25 | 78.9 | 9.1 |
| Example 27 | 85.2 | 2.9 |
| Example 29 | 92.7 | 13.4 |
| Example 30 | 73.3 | 0 |
| Example 33 | 45.2 | 0 |
| Example 34 | 87.6 | 6.9 |
| Example 35 | 86.5 | 24.5 |
| Example 37 | 40.2 | 0 |
| Example 38 | 77.6 | 17.4 |
| Example 39 | 96.6 | 23.3 |
| Example 40 | 99.5 | 47.3 |
| Example 46 | 97.6 | 11.9 |
| Example 51 | 94.7 | 16.8 |
| Example 52 | 61.2 | 0 |
| Example 53 | 89.8 | 1.0 |
| Example 58 | 93.8 | 24.0 |
| Example 63 | 91.3 | 0 |
| Example 64 | 61.5 | 20.9 |
| Example 68 | 92.7 | 31.6 |
| Example 69 | 99.0 | 36.7 |
| Example 70 | 99.9 | 63.4 |
| Example 72 | 98.6 | 44.9 |
| Example 76 | 41.7 | 0 |
| Example 77 | 88.5 | 13.8 |
| Example 78 | 36.2 | 0 |
| Example 79 | 52.9 | 0 |
| Example 82 | 31.8 | 0 |
| Example 83 | 94.4 | 39.1 |
| Example 84 | 89.5 | 0 |
| Example 87 | 97.6 | 65.1 |
| Example 91 | 84.1 | 4.8 |
| Example 92 | 95.7 | 36.5 |
| Example 94 | 99.5 | 41.2 |
| Zaleplon | 78.4 | — |

In vivo determination of predictive sedative-hypnotic action.

The in vivo effects of these compounds were assessed by a predictive sedation-hypnosis test in mice (D. J. Sanger et al., Eur. J. Pharmacol., 313, 35-42, 1996; and G. Griebel et al., Psychopharmacology, 146, 205-213, 1999). Groups of 5-8 male CD1 mice, weighing 22-26 g at the time of test, were used. The test compounds were administered in single equimolecular intraperitoneal doses, suspended in 0.25% agar with one drop of Tween in a volume of 10 ml/kg. Control animals received the vehicle alone. Using an Actisystem DAS16 (Panlab, S. L., Spain) the crossings (number of counts) were recorded for each mouse at 5-min intervals during a period of 30 minutes after dosing. The inhibition percentage of crossings of treated animals versus control animals (the first 5 min were discarded) was calculated. The results of this test are given in Table 3.

TABLE 3

Determination of sedation-hypnosis in mice.

| Compound | % Motor Activity Inhibition |
|---|---|
| Example 2 | 71.39 |
| Example 3 | 93.58 |
| Example 5 | 80.91 |
| Example 6 | 66.55 |
| Example 16 | 95.36 |
| Example 17 | 94.21 |
| Example 18 | 93.39 |
| Example 19 | 89.88 |
| Example 20 | 95.23 |
| Example 22 | 91.39 |
| Example 23 | 94.57 |
| Example 24 | 94.01 |
| Example 25 | 92.79 |
| Example 27 | 93.12 |
| Example 29 | 93.73 |
| Example 30 | 94.86 |
| Example 33 | 77.58 |
| Example 34 | 92.58 |
| Example 35 | 92.55 |
| Example 37 | 92.13 |
| Example 38 | 94.85 |
| Example 39 | 95.28 |
| Example 40 | 94.32 |
| Example 46 | 93.98 |
| Example 51 | 90.04 |
| Example 52 | 92.83 |
| Example 53 | 94.89 |
| Example 58 | 93.31 |
| Example 63 | 95.32 |
| Example 64 | 90.32 |
| Example 68 | 87.78 |
| Example 69 | 96.90 |
| Example 70 | 94.54 |
| Example 72 | 93.78 |
| Example 76 | 78.36 |
| Example 77 | 70.12 |
| Example 78 | 36.12 |
| Example 79 | 51.50 |
| Example 82 | 39.87 |
| Example 83 | 53.38 |
| Example 84 | 68.98 |
| Example 87 | 74.88 |
| Example 91 | 72.85 |
| Example 92 | 74.36 |
| Example 94 | 88.69 |
| Zaleplon | 47.17 |

The following non-limiting examples illustrate the scope of the present invention.

Example 1

N-[3-[3-(dimethylamino)-1-oxo-2-propenyl]phenyl]-N-methyl-methanesulfonamide 1.58 g (6.96 mmol) of N-(3-acetyl-phenyl)-N-methyl-methanesulfonamide were dissolved in 15 ml of N,N-dimethylformamide dimethylacetal and the resultant solution was refluxed for 18 hours. The excess of volatile reagent was removed by reduced pressure distillation to yield a crude which was chromatographied over silica gel using a gradient of ethyl acetate/methanol as eluent. 1.12 g of N-[3-[3-(dimethylamino)-1-oxo-2-propenyl]phenyl]-N-methyl methanesulfonamide as a yellowish-white solid were obtained (yield 88.6%).

$^1$H NMR (400 MHz, DMSO-d$_6$): δ 2.91 (3H, s), 2.94 (3H, s), 3.14 (3H, s), 3.26 (3H, s), 5.79 (1H, d, J=12.4 Hz), 7.44 (1H, t, J=7.6 Hz), 7.49-7.52 1H, m), 7.71 (1H, d, J=12.4 Hz), 7.78-7.81 (2H, m).

MS (ES) m/z=283 (MH$^+$)
HPLC=99.2%

Example 2

N-[3-(3-cyano-pyrazolo[1,5-a]pyrimidin-7-yl)-phenyl]-N-methyl-methanesulfonamide A mixture of 0.1 g (0.93 mmol) of 4-cyano-2H-pyrazol-3-ylamine and 0.26 g (0.93 mmol) of N-[3-[3-(dimethylamino)-1-oxo-2-propenyl]phenyl]-N-methyl-methanesulfonamide in 10 ml of glacial acetic acid was refluxed for 8 hours and then the solvent was removed by reduced pressure distillation. To the resulting residue were added 10 ml of dichloromethane and 10 ml of saturated sodium bicarbonate solution. The two layers were separated, and the aqueous layer was washed with 10 ml of dichloromethane. The organic layers were washed with 10 ml of water and dried over magnesium sulfate. The dichloromethane layer was evaporated to dryness to yield an oil which, in the presence of ethyl acetate, gave 217 mg of N-[3-(3-cyano-pyrazolo[1,5-a]pyrimidin-7-yl)-phenyl]-N-methyl-methanesulfonamide as a yellow solid (yield 71%; m.p.=193-195° C.).

$^1$H NMR (400 MHz, DMSO-d$_6$): δ 3.01 (3H, s), 3.30 (3H, s), 7.60 (1H, d, J=4.8 Hz), 7.65-7.67 (2H, m), 8.00-8.02 (1H, m), 8.09 (1H, s), 8.85 (1H, s), 8.91 (1H, d, J=4.8 Hz).

MS (ES) m/z=328 (MH$^+$)
HPLC=95.9%

Example 3

N-methyl-N-{3-[3-(thiophene-2-carbonyl)-pyrazolo[1,5-a]pyrimidin-7-yl]-phenyl}-methanesulfonamide A mixture of 0.1 g (0.52 mmol) of (5-amino-1H-pyrazol-4-yl)-thiophene-2-yl-methanone and 0.146 g (0.93 mmol) of N-[3-[3-(dimethylamino)-1-oxo-2-propenyl]phenyl]-N-methyl-methanesulfonamide (obtained as described in Example 2) in 10 ml of glacial acetic acid was refluxed for 8 hours and then the solvent was removed by reduced pressure distillation. To the resulting residue were added 10 ml of dichloromethane and 10 ml of saturated sodium bicarbonate solution. The two layers were separated, and the aqueous layer was washed with 10 ml of dichloromethane. The organic layers were washed with 10 ml of water and dried over magnesium sulfate. The dichloromethane layer was evaporated to dryness to yield an oil which, in the presence of ethyl acetate, gave 178 mg N-methyl-N-{3-[3-(thiophene-2-carbonyl)-pyrazolo[1,5-a]pyrimidin-7-yl]-phenyl}-methane-sulfonamide as a yellow solid (yield 83%; m.p.=169-170° C.).

$^1$H NMR (400 MHz, DMSO-d$_6$): δ 3.02 (3H, s), 3.32 (3H, s), 7.29 (1H, t, J=6 Hz), 7.54 (1H, d, J=4.4 Hz), 7.62-7.67 (2H, m), 8.02-8.04 (2H, m), 8.11 (1H, s), 8.20 (1H, d, J=6 Hz), 8.80 (1H, s), 8.89 (1H, d, J=4.4 Hz).

MS (ES) m/z=413 (MH+)
HPLC=99.2%

Example 4

N-[3-[3-(dimethylamino)-1-oxo-2-propenyl]phenyl]-N-ethyl-methanesulfonamide 1.1 g (4.56 mmol) of N-(3-acetyl-phenyl)-N-ethyl-methanesulfonamide were dissolved in 10 ml of N,N-dimethylformamide dimethylacetal and the resultant solution was refluxed for 18 hours. The excess of volatile reagent was removed by reduced pressure distillation to yield a crude which was chromatographied over silica gel using a gradient of ethyl acetate/methanol as eluent. 1.2 g of N-[3-[3-(dimethylamino)-1-oxo-2-propenyl]phenyl]-N-ethyl-methanesulfonamide as a yellowish-white solid were obtained (yield 88.6%)

$^1$H NMR (400 MHz, CDCl$_3$): δ 1.23 (3H, t, J=7.2 Hz), 2.88 (3H, s), 2.94 (3H, s), 3.16 (3H, s), 3.76 (2H, q, J=7.2 Hz), 5.66 (1H, d, J=12 Hz), 7.41-7.44 (2H, m), 7.79 (1H, d, J=12 Hz), 7.80-7.84 (2H, m).

HPLC=95.6%

Example 5

N-[3-(3-cyano-pyrazolo[1,5-a]pyrimidin-7-yl)-phenyl]-N-ethyl-methanesulfonamide A mixture of 0.196 g (1.82 mmol) of 4-cyano-2H-pyrazol-3-ylamine and 0.54 g (1.82 mmol) of N-[3-[3-(dimethylamino)-1-oxo-2-propenyl]phenyl]-N-ethyl-methanesulfonamide in 10 ml of glacial acetic acid was refluxed for 8 hours and then the solvent was removed by reduced pressure distillation. To the resulting residue were added 10 ml of dichloromethane and 10 ml of saturated sodium bicarbonate solution. The two layers were separated, and the aqueous layer was washed with 10 ml of dichloromethane. The organic layers were washed with 10 ml of water and dried over magnesium sulfate. The dichloromethane layer was evaporated to dryness to yield an oil which, in the presence of ethyl acetate, gave 324 mg of N-[3-(3-cyano-pyrazolo[1,5-a]pyrimidin-7-yl)-phenyl]-N-ethyl-methanesulfonamide as a yellow solid (yield 52.4%).

$^1$H NMR (400 MHz, CDCl$_3$): δ 1.21 (3H, t, J=7.2 Hz), 2.95 (3H, s), 3.81 (2H, q, J=6.8 Hz), 7.21 (1H, d, J=4.4 Hz), 7.58-7.60 (1H, m), 7.64 (1H, t, J=7.6 Hz), 7.98 (1H, d, J=7.2 Hz), 8.06 (1H, s), 8.41 (1H, s), 8.78 (1H, d, J=4 Hz).

MS (ES) m/z=342 (MH+)

HPLC=98.9%

Example 6

N-ethyl-N-{3-[3-(thiophene-2-carbonyl)-pyrazolo[1,5-a]pyrimidin-7-yl]-phenyl}-methanesulfonamide A mixture of 0.36 g (1.86 mmol) of 5-amino-1H-pyrazol-4-yl)-thiophene-2-yl-methanone and 0.55 g (1.86 mmol) of N-[3-[3-(dimethylamino)-1-oxo-2-propenyl]phenyl]-N-ethyl-methane sulfonamide in 10 ml of glacial acetic acid was refluxed for 8 hours. Thereafter, the reaction mixture was cooled and the precipitate formed, which was filtered, was washed first with acetic acid, then with saturated sodium bicarbonate solution and finally with water. 472 mg of N-ethyl-N-{3-[3-(thiophene-2-carbonyl)-pyrazolo[1,5-a]pyrimidin-7-yl]-phenyl}-methane-sulfonamide were obtained as a yellow solid (yield 59.6%).

$^1$H NMR (400 MHz, CDCl$_3$): δ 1.23 (3H, t, J=7.6 Hz), 2.97 (3H, s), 3.82 (2H, q, J=6.8 Hz), 7.17 (1H, d, J=4.4 Hz), 7.18-7.20 (1H, m), 7.57-7.60 (2H, m), 7.62 (1H, t, J=7.2 Hz), 7.69 1H, dd, J=4.8 y 1.2 Hz), 7.99-8.02 (1H, m), 8.07-8.1 (3H, m), 8.69 (1H, s), 8.80 (1H, d, J=4.4 Hz).

MS (ES) m/z=427 (MH+).

HPLC=98.3%

Example 7

N-[3-[3-(dimethylamino)-1-oxo-2-propenyl]phenyl]-N-methyl-benzenesulfonamide 1.25 g (4.32 mmol) of N-(3-acetyl-phenyl)-N-methyl-benzenesulfonamide were dissolved in 10 ml of N,N-dimethylformamide dimethylacetal and the resultant solution was refluxed for 18 hours. The excess of volatile reagent was removed by reduced pressure distillation to yield a crude which was chromatographied over silica gel using a gradient of ethyl acetate/methanol as eluent. 1.25 g of N-[3-[3-(dimethylamino)-1-oxo-2-propenyl]phenyl]-N-methyl-benzenesulfonamide as a yellowish-white solid were obtained (yield 84%).

$^1$H NMR (400 MHz, CDCl$_3$): δ 2.92 (3H, s), 3.15 (3H, s), 3.19 (3H, s), 5.58 (1H, d, J=12 Hz), 7.21-7.23 (1H, m), 7.33 (1H, t, J=8 Hz), 7.41-7.46 (2H, m), 7.52-7.58 (4H, m), 7.76 (1H, d, J=12 Hz), 7.77-7.80 (1H, m).

HPLC=100%

Example 8

N-[3-(3-cyano-pyrazolo[1,5-a]pyrimidin-7-yl)-phenyl]-N-methyl-benzenesulfonamide A mixture of 0.134 g (1.24 mmol) of 4-cyano-2H-pyrazol-3-ylamine and 0.43 g (1.24 mmol) of N-[3-[3-(dimethylamino)-1-oxo-2-propenyl]phenyl]-N-methyl-benzenesulfonamide in 10 ml of glacial acetic acid was refluxed for 8 hours and then the solvent was removed by reduced pressure distillation. To the resulting residue were added 10 ml of dichloromethane and 10 ml of saturated sodium bicarbonate solution. The two layers were separated, and the aqueous layer was washed with 10 ml of dichloromethane. The organic layers were washed with 10 ml of water and dried over magnesium sulfate. The dichloromethane layer was evaporated to dryness to yield an oil which, in the presence of ethyl acetate, gave 205 mg of N-[3-(3-cyano-pyrazolo[1,5-a]pyrimidin-7-yl)-phenyl]-N-methyl-benzenesulfonamide as a yellow solid (yield 42%).

$^1$H NMR (400 MHz, CDCl$_3$): 3.23 (3H, s) 7.13 (1H, d, J=4.8 Hz), 7.25-7.30 (1H, m), 7.45-7.63 (6H, m), 7.83 (1H, s), 7.93-7.97 (1H, m), 8.37 (1H, s), 8.75 (1H, d, J=4.4 Hz).

MS (ES) m/z=390 (MH+)

HPLC=99.0%

Example 9

N-methyl-N-{3-[3-(thiophene-2-carbonyl)-pyrazolo[1,5-a]pyrimidin-7-yl]-phenyl}-benzenesulfonamide A mixture of 0.43 g (2.23 mmol) of (5-amino-1H-pyrazol-4-yl)-thiophene-2-yl-methanone and 0.8 g (2.23 mmol) of N-[3-[3-(dimethylamino)-1-oxo-2-propenyl]phenyl]-N-methyl-methane-sulfonamide in 10 ml of glacial acetic acid was refluxed for 8 hours and then the solvent was removed by reduced pressure distillation. To the resulting residue were added 10 ml of dichloromethane and 10 ml of saturated sodium bicarbonate solution. The two layers were separated, and the aqueous layer was washed with 10 ml of dichloromethane. The organic layers were washed with 10 ml of water and dried over magnesium sulfate. The dichloromethane layer was evaporated to dryness to yield an oil which, in the presence of ethyl acetate, gave 872 g of N-methyl-N-{3-[3-(thiophene-2-carbonyl)-pyrazolo[1,5-a]pyrimidin-7-yl]-phenyl}-benzenesulfonamide as a yellow solid (yield 82.3%).

$^1$H NMR (400 MHz, CDCl$_3$): δ 3.24 (3H, s), 7.07 (1H, d, J=4.4 Hz), 7.19 (1H, t, J=4 Hz), 7.28-7.31 (1H, m), 7.46-7.62 (6H, m), 7.7 (1H, d, J=5.2 Hz), 7.82 (1H, t, J=2 Hz), 7.97 (1H, d, J=6.8 Hz), 8.09 (1H, d, J=3.6 Hz), 8.66 (1H, s), 8.79 (1H, d, J=4.4 Hz).

MS (ES) m/z=475 (MH+)
HPLC=97.9%

Example 10

N-[3-[3-(dimethylamino)-1-oxo-2-propenyl]phenyl]-N-ethyl-benzenesulfonamide 1.05 g (3.46 mmol) of N-(3-acetyl-phenyl)-N-ethyl-benzenesulfonamide were dissolved in 10 ml of N,N-dimethylformamide dimethylacetal and the resultant solution was refluxed for 18 hours. The excess of volatile reagent was removed by reduced pressure distillation to yield a crude which was chromatographied over silica gel using a gradient of ethyl acetate/methanol as eluent. 1.2 g of N-[3-[3-(dimethylamino)-1-oxo-2-propenyl]phenyl]-N-ethyl-benzenesulfonamide as a yellowish-white solid were obtained (yield 96%).

$^1$H NMR (400 MHz, CDCl$_3$): δ 1.06 (3H, t, J=7.2 Hz), 2.92 (3H, s), 3.15 (3H, s), 3.62 (2H, q, J=7.6 Hz), 5.56 (1H, d, J=12.4 Hz), 7.14-7.17 (1H, m), 7.35 (1H, t, J=7.6 Hz), 7.42-7.49 (3H, m), 7.52-7.60 (3H, m), 7.76 (1H, d, J=12.4 Hz), 7.81 (1H, d, J=8 Hz).
HPLC=100%

Example 11

N-[3-(3-cyano-pyrazolo[1,5-a]pyrimidin-7-yl)-phenyl]-N-ethyl-benzenesulfonamide

A mixture of 0.15 g (1.38 mmol) of 4-cyano-2H-pyrazol-3-ylamine and 0.50 g (1.38 mmol) of N-[3-[3-(dimethylamino)-1-oxo-2-propenyl]phenyl]-N-ethyl-benzenesulfonamide in 10 ml of glacial acetic acid was refluxed for 8 hours and then the solvent was removed by reduced pressure distillation. To the resulting residue were added 10 ml of dichloromethane and 10 ml of saturated sodium bicarbonate solution. The two layers were separated, and the aqueous layer was washed with 10 ml of dichloromethane. The organic layers were washed with 10 ml of water and dried over magnesium sulfate. The dichloromethane layer was evaporated to dryness to yield an oil which, in the presence of ethyl acetate, gave 260 mg of N-[3-(3-cyano-pyrazolo[1,5-a]pyrimidin-7-yl)-phenyl]-N-ethyl-benzenesulfonamide as a yellow solid (yield 47%).

$^1$H NMR (400 MHz, CDCl$_3$): δ 1.14 (3H, t, J=6.8 Hz), 3.66 (2H, q, J=7.2 Hz), 7.12 (1H, d, J=4.8 Hz), 7.26 (1H, d, J=7.6 Hz), 7.46-7.65 (6H, m), 7.76 (1H, s), 8.02 (1H, d, J=7.6 Hz), 8.38 (1H, s), 8.76 (1H, d, J=4.4 Hz).
MS (ES) m/z=404 (MH+)
HPLC=98.9%

Example 12

N-ethyl-N-{3-[3-(thiophene-2-carbonyl)-pyrazolo[1,5-a]pyrimidin-7-yl]-phenyl}-benzenesulfonamide A mixture of 0.33 g (1.70 mmol) of (5-amino-1H-pyrazol-4-yl)-thiophene-2-yl-methanone and 0.61 g (1.70 mmol) of N-[3-[3-(dimethylamino)-1-oxo-2-propenyl]phenyl]-N-ethyl-benzenesulfonamide in 10 ml of glacial acetic acid was refluxed for 8 hours and then the solvent was removed by reduced pressure distillation. To the resulting residue were added 10 ml of dichloromethane and 10 ml of saturated sodium bicarbonate solution. The two layers were separated, and the aqueous layer was washed with 10 ml of dichloromethane. The organic layers were washed with 10 ml of water and dried over magnesium sulfate. The dichloromethane layer was evaporated to dryness to yield an oil which, in the presence of ethyl acetate, gave 535 mg of N-ethyl-N-{3-[3-(thiophene-2-carbonyl)-pyrazolo[1,5-a]pyrimidin-7-yl]-phenyl}-benzenesulfonamide as a yellow solid (yield 64.4%).

$^1$H NMR (400 MHz, CDCl$_3$): δ 1.15 (3H, t, J=7.6 Hz), 3.67 (2H, q, J=7.6 Hz), 7.07 (1H, d, J=4.4 Hz), 7.18-7.21 (1H, m), 7.27-7.30 (1H, m), 7.51 (2H, t, J=7.6 Hz), 7.56 (1H, t, J=7.6 Hz), 7.60-7.67 (4H, m), 7.69 (1H, dd, J=5.2 Hz y J=1.2 Hz), 7.75 (1H, t, J=2 Hz), 8.06 (1H, d, J=7.6 Hz), 8.09 (1H, d, J=3.6 Hz), 8.67 (1H, s), 8.79 (1H, d, J=4.4 Hz).
MS (ES) m/z=489 (MH+)
HPLC=97.9%

Example 13

General Procedure for the Preparation of N-Methyl-Enamine-Sulfonamides of General Formula (VI) Following Scheme 2

N-[3-[3-(dimethylamino)-1-oxo-2-propenyl]phenyl]-N-ethyl-ethanesulfonamide 2 g (8.8 mmol) of N-(3-acetyl-phenyl)-ethanesulfonamide were dissolved in 15 ml of N,N-dimethylformamide dimethyl acetal and heated at 150° C. for 12 h. The solvent was removed by reduced pressure distillation to yield a crude which was chromatographied (silica gel) using ethyl acetate/methanol as eluent. 1.4 g (yield=56%) of N-[3-[3-(dimethylamino)-1-oxo-2-propenyl]phenyl]-ethanesulfonamide were obtained.

0.25 g (0.89 mmol) of N-[3-[3-(dimethylamino)-1-oxo-2-propenyl]phenyl]-ethanesulfonamide were dissolved in 6 ml of dry N,N-dimethylformamide. To the solution formed at 0° C. and under inert atmosphere, 0.043 g (1.08 mmol) of sodium hydride were added. After stirring for 30 minutes, 0.15 g (0.98 mmol) of ethyl iodide were added and stirring was maintained at room temperature for 5 h. To the reaction mixture 1 ml of water and then 20 ml of 0.5M NaOH were added. The product was separated by extraction with 3×25 ml of dichloromethane, and the organic layers were washed with 25 ml of water, dried over anhydrous sodium sulfate, filtered off and evaporated to dryness by reduced pressure distillation. 0.25 g (yield=90%) of N-{3-[3-(dimethylamino)-1-oxo-2-propenyl]phenyl}-N-ethyl-ethane-sulfonamide were obtained as an oil.

$^1$H NMR (400 MHz, CDCl$_3$): δ 1.12 (3H, t, J=6.8 Hz), 1.37 (3H, t, J=7.6 Hz), 2.94 (3H, s), 3.01 (2H, q, J=7.6 Hz), 3.15 (3H, s), 4.79 (2H, q, J=8.2 Hz), 5.66 (1H, d, J=12.4 Hz), 7.39-7.46 (2H, m), 7.77-7.84 (3H, m)
HPLC=99%

As described in the above general procedure, the following compounds were prepared:

N-[3-[3-(dimethylamino)-1-oxo-2-propenyl]phenyl]-N-ethyl-isopropanesulfonamide $^1$H NMR (400 MHz, CDCl$_3$): δ 1.12 (3H, t, J=7.2 Hz), 1.37 (6H, d, J=6.8 Hz), 2.95 (3H, s), 3.18 (3H, s), 3.18-3.25 (1H, m), 3.82 (2H, q, J=7.6 Hz), 5.67 (1H, d, J=12.4 Hz), 7.39-7.49 (2H, m), 7.78-7.81 (2H, m), 7.85-7.87 (1H, m)
HPLC=99.4%

N-[3-[3-(dimethylamino)-1-oxo-2-propenyl]phenyl]-N-propyl-methanesulfonamide $^1$H NMR (400 MHz, DMSO-d$_6$): δ 0.83 (3H, t, J=7.6 Hz), 1.31-1.36 (2H, m), 2.49 (3H, s), 2.91 (3H, s), 3.14 (3H, s), 3.61 (2H, t, J=7.2 Hz), 7.78 (1H, d, J=12 Hz), 7.42-7.51 (2H, m), 7.71 (1H, d, J=12.4 Hz), 7.77-7.78 (1H, m), 7.82-7.85 (1H, m)
HPLC=88.8%

N-[3-[3-(dimethylamino)-1-oxo-2-propenyl]phenyl]-N-propyl-ethanesulfonamide $^1$H NMR (400 MHz, CDCl$_3$): δ 0.89 (3H, t, J=7.6 Hz), 1.37 (3H, t, J=7.6 Hz), 1.42-1.51 (2H, m), 2.71 (1H, s), 2.94 (3H, s), 3.02 (2H, q, J=7.6 Hz), 3.16 (3H, s, J=12.4 Hz), 3.69 (2H, t, J=7.2 Hz), 7.39-7.47 (2H, m), 7.78-7.85 (3H, m)
HPLC=98%

N-[3-[3-(dimethylamino)-1-oxo-2-propenyl]phenyl]-N-propyl-isopropanesulfonamide $^1$H NMR (400 MHz, CDCl$_3$): δ 0.88 (3H, t, J=7.2 Hz), 1.37 (6H, d, J=6.8 Hz), 1.45-1.51 (2H, m), 2.94 (3H, s), 3.17 (3H, s), 3.17-3.24 (1H, m), 3.73 (2H, t, J=7.6 Hz), 5.67 (1H, d, J=12.8 Hz), 7.41 (1H, t, J=8 Hz), 7.48-7.51 (1H, m), 7.77-7.87 (3H, m)
HPLC=99.6%

N-[3-[3-(dimethylamino)-1-oxo-2-propenyl]phenyl]-N-butyl-methane sulfonamide $^1$H NMR (400 MHz, CDCl$_3$): δ 0.81 (3H, t, J=7.6 Hz), 1.25-1.31 (4H, m), 2.92 (3H, s), 3.14 (3H, s), 3.64 (2H, t, J=6.8 Hz), 5.78 (1H, d, J=12 Hz), 7.44-7.50 (2H, m), 7.71 (1H, d, J=12 Hz), 7.76-7.77 (1H, m), 7.82-7.85 (1H, m)
HPLC=98%

N-[3-[3-(dimethylamino)-1-oxo-2-propenyl]phenyl]-N-butyl-ethanesulfonamide $^1$H NMR (400 MHz, CDCl$_3$): δ 0.86 (3H, t, J=7.6 Hz), 1.3-1.46 (7H, m), 2.94 (3H, s), 3.01 (2H, q, J=7.2 Hz), 3.17 (3H, s), 3.73 (2H, t, J=7.6 Hz), 5.63 (1H, d), 7.39-7.47 (2H, m), 7.78-7.85 (3H, m)
HPLC=98.1%

N-[3-[3-(dimethylamino)-1-oxo-2-propenyl]phenyl]-N-butyl-isopropanesulfonamide $^1$H NMR (400 MHz, CDCl$_3$): δ 0.86 (3H, t, J=7.6 Hz), 1.28-1.34 (2H, m), 1.36 (6H, d, J=7.2 Hz), 1.41-1.45 (2H, m), 2.94 (3H, s), 3.16-3.24 (4H, m), 3.76 (2H, t, J=7.2 Hz), 5.67 (1H, d, J=12.4 Hz), 7.41 (1H, t, J=8 Hz), 7.47-7.51 (1H, m) 7.78-7.82 (2H, m) 7.86-7.88 (1H, m)
HPLC=99.4%

N-[3-[3-(dimethylamino)-1-oxo-2-propenyl]phenyl]-N-propargyl-methanesulfonamide $^1$H NMR (400 MHz, CDCl$_3$): δ 2.5 (1H, t, J=2.8 Hz), 2.94 (3H, s), 3.05 (3H, s), 3.17 (3H, s), 4.46 (2H, s), 5.67 (1H, d, J=12.4 Hz), 7.44 (1H, t, J=8 Hz), 7.63-7.66 (1H, m), 7.81 (1H, m, J=12 Hz), 7.84-7.87 (1H, m) 8.09 (1H, t, J=2 Hz)
HPLC=98.8%

N-[3-[3-(dimethylamino)-1-oxo-2-propenyl]phenyl]-N-propargyl-ethanesulfonamide $^1$H NMR (400 MHz, CDCl$_3$): δ 1.39 (3H, t, J=7.2 Hz), 2.4 (1H, t, J=2.8 Hz), 2.94 (3H, s), 3.14-3.22 (5H, m), 4.47 (2H, d, J=2.4 Hz), 5.66 (1H, d, J=12.4 Hz), 7.42-7.44 (2H, m), 7.61-7.64 (1H, m), 7.78-7.85 (3H, m), 8.05 (1H, t, J=2 Hz)
MS (ES) m/z=321 (MH+)

N-[3-[3-(dimethylamino)-1-oxo-2-propenyl]phenyl]-N-propargyl-isopropanesulfonamide $^1$H NMR (400 MHz, CDCl$_3$): δ 1.4 (6H, d, J=6.4 Hz), 2.37 (1H, t, J=2.4 Hz), 2.94 (3H, s), 3.17 (3H, s), 3.34-3.41 (1H, m), 4.49 (2H, d, J=2.8 Hz), 5.66 (1H, d, J=12.4 Hz), 7.40-7.44 (1H, m), 7.59-7.62 (1H, m), 7.78-7.87 (2H, m), 7.99-8.00 (1H, m)
HPLC=81%

Example 14

General Procedure for the Preparation of N-Methyl-Enamine-Sulfonamides of General Formula (VII) Following Scheme 3

N-(3-acetylphenyl)-1-propane-sulfonamide 1 g (7.4 mmol) of 3-aminoacetophenone were dissolved in 35 ml of dry dichloromethane. To the resultant solution cooled at 0° C. 0.89 ml (11.09 mmol) of anhydrous pyridine and 1.26 g (8.87 mmol) of 1-propanesulfonic acid chloride were added. After stirring the reaction mixture for 20 h at room temperature and under inert atmosphere, 15 ml of water were added. The two layers were separated, and the aqueous layer was washed with 2×15 ml of dichloromethane. The organic layers were washed with 30 ml of water and dried over anhydrous sodium sulfate. The dichloromethane layer was evaporated to dryness to yield a yellow solid, 1.8 g (yield=100%) of N-(3-acetylphenyl)-1-propane-sulfonamide which was directly used for the following reaction.

N-[3-[3-(dimethylamino)-1-oxo-2-propenyl]phenyl]-N-methyl-1-propanesulfonamide 1 g (4.14 mmol) of N-(3-acetylphenyl)-1-propane-sulfonamide were dissolved in 10 ml of N,N-dimethylformamide. To the resultant solution 2.77 ml (20.74 mmol) of N,N-dimethylformamide dimethyl acetal were added and heated at 150° C. for 2 h. The solvent was removed by reduced pressure distillation to yield an oil, which was treated with a mixture of ethyl acetate-ethyl ether. A small quantity of a solid precipitated which was discarded. The filtrate was evaporated to dryness, dissolved in dichloromethane, and the organic layer was washed with 4×50 ml of water and evaporated to dryness. 1.23 g (yield=96%) of N-[3-[3-(dimethylamino)-1-oxo-2-propenyl]phenyl]-N-methyl-1-propane-sulfonamide were obtained.

$^1$H NMR (400 MHz, CDCl$_3$): δ 0.99 (3H, t, J=7.6 Hz), 1.75-1.90 (2H, m), 2.91-2.97 (5H, m), 3.15 (3H, a), 3.35 (3H, s), 5.66 (1H, d, J=12.5 Hz), 7.36-7.52 (2H, m), 7.73-7.88 (3H, m)

As described in the above general procedure, the following compounds were prepared:

N-[3-[3-(dimethylamino)-1-oxo-2-propenyl]phenyl]-N-methyl-butanesulfonamide $^1$H NMR (400 MHz, CDCl$_3$): δ 0.92 (3H, t, J=7.4 Hz), 1.35-1.5 (2H, m), 1.75-1.87 (2H, m), 2.97-3.03 (5H, m), 3.18 (3H, a), 3.39 (3H, s), 5.7 (1H, d, J=12.2 Hz), 7.39-7.46 (1H, m), 7.52-7.56 (1H, m), 7.77-7.87 (1H, m), 7.83 (1H, d, J=12.2 Hz), 7.9-7.91 (1H, m)

N-[3-[3-(dimethylamino)-1-oxo-2-propenyl]phenyl]-
N-methyl-cyclopentylmethanesulfonamide ¹H NMR (400 MHz, CDCl₃): δ 1.22-1.3 (2H, m), 1.55-1.63 (4H, m), 1.91-1.98 (2H, m), 2.27-2.4 (1H, m), 2.86-2.93 (5H, m), 3.15 (3H, a), 3.34 (3H, s), 5.67 (1H, d, J=12.5 Hz), 7.37-7.52 (2H, m), 7.44-7.98 (3H, m)

Example 15

General Procedure for the Preparation of
N-Methyl-Enamine-Sulfonamides of General
Formula (VII) Following Scheme 4

N-(3-acetylphenyl)-2,2,2-trifluoroacetamide 5 g (37 mmol) of 3-aminoacetophenone were dissolved in 30 ml of anhydrous dichloromethane. To the resultant solution 3.15 ml (38.84 mmol) of anhydrous pyridine and 5.5 ml (38.84 mmol) of trifluoroacetic anhydride were added at 0° C. The reaction mixture was stirred for 30 minutes at the same temperature and poured onto 100 ml of water-ice. 100 ml of a saturated solution of sodium chloride were added and extracted with 2×70 ml of dichloromethane and 3×50 ml of ethyl acetate. The organic layers were washed with water, dried over anhydrous sodium sulfate and evaporated to dryness by reduced pressure distillation. 8.7 g (yield=100%) as a solid of N-(3-acetylphenyl)-2,2,2-trifluoroacetamide were obtained.
¹H NMR (400 MHz, CDCl₃): δ 2.64 (3H, s), 7.53 (1H, t, J=7.6 Hz), 7.82 (1H, d, J=7.6 Hz), 8.15 (1H, d, J=8.2 Hz), 8.25 (1H, s), 9.12 (1H, a)

3-(dimethylamino)-1-[3-(methylamino)phenyl]prop-
2-en-1-one 8.37 g (36.21 mmol) de N-(3-acetylphenyl)-2,2,2-trifluoro-acetamide were dissolved in 80 ml of N,N-dimethyl formamide. To the resultant solution 24.23 ml (181.02 mmol) of N,N-dimethylformamide dimethyl acetal were added and heated at 150° C. for 2 h. The solvent was removed by reduced pressure distillation to yield an oil which was treated with 50 ml of water and extract with 3×100 ml of dichloromethane. The organic layers were washed with 2×200 ml of a saturated solution of sodium chloride, dried over anhydrous sodium sulfate and evaporated to dryness by reduced pressure distillation. A solid was obtained, which precipitated from a mixture of ethanol-ethyl ether to give 4.1 g (yield=55%) of 3-(dimethylamino)-1-[3-(methylamino)phenyl]prop-2-en-1-one.
¹H NMR (400 MHz, CDCl₃): δ 2.85 (3H, s), 2.87 (3H, s), 3.11 (3H, s), 3.85 (1H, a), 5.68 (1H, d, J=12.2 Hz), 6.67-6.72 (1H, m), 7.16-7.24 (3H, m), 7.77 (1H, d, J=12.2 Hz)

N-[3-[3-(dimethylamino)-1-oxo-2-propenyl]phenyl]-
N-methyl-2-phenyl-ethylenesulfonamide 0.4 g (1.96 mmol) of 3-(dimethylamino)-1-[3-(methylamino)phenyl]prop-2-en-1-one were dissolved in 15 ml of dry dichloromethane. To the resultant solution 0.24 ml (2.01 mmol) of anhydrous pyridine and 0.48 g (2.37 mmol) of 2-phenyl-ethene-sulfonic acid chloride were added. After stirring the reaction mixture for 17 h at room temperature and under inert atmosphere, 15 ml of water were added. The two layers were separated, and the aqueous layer was washed with 2×15 ml of dichloromethane. The organic layers were washed with 30 ml of water and dried over anhydrous sodium sulfate. The dicholoromethane layer was evaporated to dryness to yield a crude which was chromatographied (silica gel) using dichloromethane-methanol as eluent. 0.53 (yield=73%) of a solid, N-[3-[3-(dimethylamino)-1-oxo-2-propenyl]phenyl]-N-methyl-2-phenyl-ethylene-sulfonamide, were obtained.
¹H NMR (400 MHz, CDCl₃): δ 2.9 (3H, a), 3.16 (3H, a), 3.31 (3H, s), 5.65 (1H, d, J=12.5 Hz), 6.7 (1H, d, J=15.5 Hz), 7.38-7.5 (8H, m), 7.77-7.85 (3H, m)

As described in the above general procedure the following compounds were prepared:

N-[3-[3-(dimethylamino)-1-oxo-2-propenyl]phenyl]-
N-methyl-3-chlorobenzenesulfonamide ¹H NMR (400 MHz, CDCl₃): δ 2.93 (3H, a), 3.16 (3H, a), 3.22 (3H, s), 5.6 (1H, d), 7.23-7.27 (1H, m), 7.35-7.41 (3H, m), 7.52-7.58 (3H, m), 7.76 (1H, s), 7.79-7.83 (1H, m)

N-[3-[3-(dimethylamino)-1-oxo-2-propenyl]phenyl]-
N-methyl-4-chlorobenzenesulfonamide ¹H NMR (400 MHz, CDCl₃): d 2.94 (3H, a), 3.18 (3H, a), 3.2 (3H, a), 5.59 (1H, d, J=12.2 Hz), 7.23-7.29 (1H, m), 7.34-7.55 (6H, m), 7.77-7.83 (2H, m)

N-[3-[3-(dimethylamino)-1-oxo-2-propenyl]phenyl]-
N-methyl-2-chlorobenzenesulfonamide ¹H NMR (400 MHz, CDCl₃): δ 2.73 (3H, a), 2.96 (3H, a), 3.24 (3H, s), 5.6 (1H, d, J=12.5 Hz), 7.06-7.14 (3H, m), 7.21-7.32 (2H, m), 7.5-7.6 (3H, m), 7.68 (1H, dd), J=7.9 Hz, J=1.5 Hz)

N-[3-[3-(dimethylamino)-1-oxo-2-propenyl]phenyl]-
N-methyl-2,2,2-trifluoroethanesulfonamide ¹H NMR (400 MHz, CDCl₃): δ 2.95 (3H, a), 3.18 (3H, s), 3.42 (3H, s), 3.73 (2H, c, J=9.1 Hz), 5.66 (1H, d, J=12.2 Hz), 7.42-7.53 (2H, m), 7.8 (1H, s), 7.83-7.89 (2H, m)

N-[3-[3-(dimethylamino)-1-oxo-2-propenyl]phenyl]-
N-methyl-2,4-dichlorobenzenesulfonamide ¹H NMR (400 MHz, CDCl₃): δ 2.96 (3H, a), 3.19 (3H, s), 3.46 (3H, s), 5.6 (1H, d, J=12.2 Hz), 7.27 (1H, d, J=2.1 Hz), 7.31 (1H, d, J=1.8 Hz), 7.34-7.38 (1H, m), 7.53 (1H, d, J=2.1 Hz), 7.71-7.84 (4H, m)

N-[3-[3-(dimethylamino)-1-oxo-2-propenyl]phenyl]-N-methyl-3,4-dichlorobenzenesulfonamide
¹H NMR (400 MHz, CDCl₃): δ 2.86 (3H, s), 3.09 (3H, s), 3.15 (3H, s), 5.52 (1H, d, J=12.2 Hz), 7.16-7.23 (1H, m), 7.26 (1H, d, J=2.1 Hz), 7.32 (1H, t, J=7.9 Hz), 7.45 (1H, d, J=8.5 Hz), 7.49 (1H, m), 7.61 (1H, d, J=2.1 Hz)

N-[3-[3-(dimethylamino)-1-oxo-2-propenyl]phenyl]-
N-methyl-2-cyanobenzenesulfonamide ¹H NMR (400 MHz, CDCl₃): δ 2.97 (3H, a), 3.19 (3H, a), 3.43 (3H, s), 5.64 (1H, d, J=12.2 Hz), 7.35 (1H, m), 7.41 (1H, t, J=7.9 Hz), 7.6-7.89 (7H, m)

N-[3-[3-(dimethylamino)-1-oxo-2-propenyl]phenyl]-
N-methyl-3-cyanobenzenesulfonamide ¹H NMR (400 MHz, CDCl₃): δ 2.94 (3H, a), 3.16 (3H, a), 3.23 (3H, s), 5.62 (1H, d, J=12.2 Hz), 7.24-7.29 (1H, m), 7.39 (1H, t, J=7.6 Hz), 7.5 (1H, m), 7.55-7.62 (1H, m), 7.69-7.86 (5H, m)

N-[3-[3-(dimethylamino)-1-oxo-2-propenyl]phenyl]-N-methyl-4-cyanobenzenesulfonamide $^1$H NMR (400 MHz, CDCl$_3$): δ 2.94 (3H, a), 3.17 (3H, a), 3.22 (3H, s), 5.6 (1H, d, J=12.2 Hz), 7.24-7.3 (1H, m), 7.39 (1H, t, J=7.9 Hz), 7.51 (1H, m), 7.64-7.7 (2H, m), 7.73-7.82 (4H, m)

N-[3-[3-(dimethylamino)-1-oxo-2-propenyl]phenyl]-N-methyl-3-nitrobenzenesulfonamide $^1$H NMR (400 MHz, CDCl$_3$): δ 2.93 (3H, a), 3.16 (3H, a), 3.26 (3H, s), 5.6 (1H, d, J=12.2 Hz), 7.27-7.32 (2H, m), 7.39 (1H, t, J=7.9 Hz), 7.48 (1H, m), 7.62-7.82 (4H, m), 8.4-8.44 (1H, m)

N-[3-[3-(dimethylamino)-1-oxo-2-propenyl]phenyl]-N-methyl-4-nitrobenzenesulfonamide $^1$H NMR (400 MHz, CDCl$_3$): δ 2.92 (3H, a), 3.17 (3H, a), 3.25 (3H, s), 5.6 (1H, d, J=12.5 Hz), 7.25-7.29 (1H, m), 7.39 (1H, t, J=7.9 Hz), 7.53 (1H, m), 7.73 (2H, d, J=9 Hz), 8.4-8.44 (1H, m), 7.77-7.84 (2H, m), 8.3 (2H, d, J=9 Hz)

N-[3-[3-(dimethylamino)-1-oxo-2-propenyl]phenyl]-N-methyl-2-thiophenesulfonamide $^1$H NMR (400 MHz, CDCl$_3$): δ 2.85 (3H, a), 3.07 (3H, a), 3.19 (3H, s), 5.54 (1H, d, J=12.5 Hz), 6.99 (1H, dd, J=4.8 Hz), 7.19-7.32 (3H, m), 7.48-7.53 (2H, m), 7.67-7.74 (2H, m)

N-[3-[3-(dimethylamino)-1-oxo-2-propenyl]phenyl]-N-methyl-5-methyl-4-isoxazolesulfonamide $^1$H NMR (400 MHz, CDCl$_3$): δ 2.13 (3H, s), 2.88 (3H, a), 3.11 (3H, s), 3.19 (3H, m), 5.53 (1H, d, J=12.5 Hz), 7.21-7.28 (1H, m), 7.35 (1H, t, J=7.9 Hz), 7.56-7.81 (3H, m), 8.15 (1H, m)

N-[3-[3-(dimethylamino)-1-oxo-2-propenyl]phenyl]-N-methyl-2-trifluoromethyl-5-methyl-3-furansulfonamide $^1$H NMR (400 MHz, CDCl$_3$): δ 2.13 (3H, s), 2.94 (3H, a), 3.27 (3H, s), 5.61 (1H, d, J=12.2 Hz), 6.8 (1H, m), 7.3-7.44 (2H, m), 7.66 (1H, t), 7.79-7.86 (2H, m)

N-[3-[3-(dimethylamino)-1-oxo-2-propenyl]phenyl]-N-methyl-6-(morpholin-4-yl)-3-pyridinesulfonamide $^1$H NMR (400 MHz, CDCl$_3$): δ 2.88 (3H, a), 3.13 (3H, s), 3.54-3.58 (4H, m), 3.71-3.75 (4H, m), 5.59 (1H, d, J=12.5 Hz), 6.43 (1H, dd, J=9.1 Hz), 7.21-7.3 (2H, m), 7.35 (1H, dd, J=9.1 Hz), 7.58-7.6 (1H, m), 7.69-7.74 (2H, m), 8.3 (1H, dd, J=2.6 y 0.8 Hz)

N-[3-[3-(dimethylamino)-1-oxo-2-propenyl]phenyl]-N-methyl-2,4-dimethyl-5-thiazolesulfonamide $^1$H NMR (400 MHz, CDCl$_3$): δ 2.06 (3H, s), 2.6 (3H, s), 2.88 (3H, a), 3.1 (3H, a), 3.23 (3H, s), 5.56 (1H, dd, J=12.2 Hz), 7.23-7.38 (2H, m), 7.7-7.8 (3H, m)

N-[3-[3-(dimethylamino)-1-oxo-2-propenyl]phenyl]-N-methyl-cyclopropanesulfonamide $^1$H NMR (400 MHz, CDCl$_3$): δ 1.03-1.12 (1H, m), 1.23-1.32 (1H, m), 1.5-1.54 (1H, m), 2.26-2.37 (1H, m), 2.88 (3H, a), 3.09 (3H, a), 3.16-3.28 (1H, m), 3.31 (3H, s), 5.62 (1H, d, J=12.2 Hz), 7.3-7.37 (1H, m), 7.44-7.48 (1H, m), 7.7-7.77 (2H, m), 7.87-7.88 (1H, m)

N-[3-[3-(dimethylamino)-1-oxo-2-propenyl]-phenyl]-N-methyl-benzylsulfonamide $^1$H NMR (400 MHz, CDCl$_3$): δ 3.05 (3H, a), 3.25 (6H, s), 4.37 (2H, s), 5.76 (1H, d, J=12.2 Hz), 7.44-7.51 (7H, m), 7.83-7.93 (3H, m)

N-[3-[3-(dimethylamino)-1-oxo-2-propenyl]phenyl]-N-methyl-vinylsulfonamide $^1$H NMR (400 MHz, CDCl$_3$): δ 2.92 (3H, a), 3.14 (3H, a), 5.66 (1H, d, J=12.2 Hz), 5.97 (1H, dd), 6.13 (1H, dd), 6.39 (1H, dd), 7.31-7.47 (2H, m), 7.7-7.75 (2H, m), 7.87 (1H, d, J=12.2 Hz)

N-[3-[3-(dimethylamino)-1-oxo-2-propenyl]phenyl]-N-methyl 3,5-dimethyl-4-isoxazolesulfonamide $^1$H NMR (400 MHz, CDCl$_3$): δ 2.03 (3H, s), 2.27 (3H, s), 2.94 (3H, a), 3.16 (3H, a), 3.27 (3H, s), 5.58 (1H, d, J=12.2 Hz), 7.31-7.43 (2H, m), 7.66 (1H, m), 7.77-7.85 (2H, m)

N-[3-[3-(dimethylamino)-1-oxo-2-propenyl]phenyl]-N-methyl 1,3,5-trimethyl-4-pyrazolesulfonamide $^1$H NMR (400 MHz, CDCl$_3$): δ 1.96 (3H, s), 2.84 (3H, a), 3.16 (3H, a), 3.2 (3H, a), 3.68 (3H, s), 5.63 (1H, d, J=12.5 Hz), 7.34-7.37 (2H, m), 7.63 (1H, m), 7.76-7.82 (2H, m)

Example 16

General Procedure for the Preparation of pyrazolo[1,5-a]pyrimidines of General Formula (I) Following Scheme 1

N-2-propynyl-N-{3-[3-(thiophene-2-carbonyl)-pyrazolo[1,5-a]pyrimidin-7-yl]-phenyl}-methanesulfonamide 0.1 g (0.33 mmol) of 4-thiophene-2-carbonyl-2H-pyrazol-3-ylamine and 0.063 g (0.33 mmol) of N-[3-[3-(dimethylamino)-1-oxo-2-propenyl]phenyl]-N-2-propynyl-methanesulfonamide were dissolved in 10 ml of glacial acetic acid. After refluxing for 8 hours, the solvent was removed by reduced pressure distillation. To the resultant residue 10 ml of dichloromethane and 10 ml of a saturated solution of sodium bicarbonate were added. The two layers were separated, and the aqueous layer was washed with 10 ml of dichloromethane. The organic layers were washed with 10 ml of water and dried over magnesium sulfate. The dichloromethane layer was evaporate to dryness to yield an oil which, in the presence of ethyl acetate gave a yellow solid, 111 mg (yield=78%) N-2-propynyl-N-{3-[3-(thiophene-2-carbonyl)-pyrazolo[1,5-a]pyrimidin-7-yl]-phenyl}-methanesulfonamide.

$^1$H NMR (400 MHz, CDCl$_3$): δ 2.54 (1H, s), 3.12 (3H, s), 4.54 (2H, s), 7.15 (1H, d, J=4 Hz), 7.19-7.21 (1H, m), 7.65 (1H, t, J=7.6 Hz), 7.69-7.71 (1H, m), 7.84-7.87 (1H, m), 8.03-8.06 (1H, m), 8.08-8.10 (1H, m) 8.31 (1H, t, J=2 Hz) 8.71 (1H, s) 8.82 (1H, d, J=4.4 Hz)

MS (ES) m/z=437 (MH+)

HPLC=100%

As described in the general procedure of Example 16, the following exemplified compounds were prepared:

Example 17

N-propyl-N-{3-[3-(thiophene-2-carbonyl)-pyrazolo[1,5-a]pyrimidin-7-yl]-phenyl}-ethanesulfonamide $^1$H NMR (400 MHz, CDCl$_3$): δ 0.94 (3H, t, J=7.6 Hz), 1.42 (3H, t, J=7.6 Hz), 1.54-1.63 (2H, m), 3.08-3.31 (2H, m), 3.75 (2H, t, J=7.2 Hz), 7.16 (1H, d, J=4.4 Hz), 7.19-7.21 (1H, m), 7.59-7.65 (2H, m), 7.69-7.71 (1H, m), 7.99-8.02 (1H, m) 8.09-8.11 (2H, m, J=2 Hz) 8.71 (1H, s) 8.82 (1H, d, J=4.4 Hz)
MS (ES) m/z=455 (MH+)
HPLC=97.86%

Example 18

N-ethyl-N-{3-[3-(thiophene-2-carbonyl)-pyrazolo[1,5-a]pyrimidin-7-yl]-phenyl}-ethanesulfonamide $^1$H NMR (400 MHz, CDCl$_3$): δ 1.22 (3H, t, J=6.8 Hz), 1.43 (3H, t, J=7.6 Hz), 3.11 (2H, c, J=7.6 Hz), 3.85 (2H, c, J=6.8 Hz), 7.16 (1H, d, J=4.4 Hz), 7.19-7.21 (1H, m, J=4.4 Hz), 7.58-7.66 (2H, m), 7.69-7.71 (1H, m), 7.99-8.02 (1H, m), 8.09-8.11 (2H, m) 8.71 (1H, s) 8.82 (1H, d, J=4.4 Hz)
MS (ES) m/z=441 (MH+)
HPLC=97.73%

Example 19

N-2-propynyl-N-{3-[3-(thiophene-2-carbonyl)-pyrazolo[1,5-a]pyrimidin-7-yl]-phenyl}-2-propane-sulfonamide $^1$H NMR (400 MHz, CDCl$_3$): δ 1.44 (6H, d, J=6.4 Hz), 2.42 (1H, m), 3.44-3.51 (1H, m), 4.56 (1H, s), 7.15 (1H, d, J=4 Hz), 7.19-7.20 (1H, m), 7.65 (1H, t, J=8 Hz), 7.69-7.71 (1H, m), 7.76-7.79 (1H, m), 8.02-8.05 (1H, m) 8.09-8.11 (1H, m) 8.24-8.25 (1H, m) 8.7 (1H, s) 8.82 (1H, d, J=4.4 Hz)
MS (ES) m/z=465 (MH+)
HPLC=100%

Example 20

N-methyl-N-{3-[3-(thiophene-2-carbonyl)-pyrazolo[1,5-a]pyrimidin-7-yl]-phenyl}-ethanesulfonamide $^1$H NMR (400 MHz, CDCl$_3$): δ 1.41 (3H, t, J=7.2 Hz), 3.12 (2H, c, J=7.6 Hz), 3.45 (3H, s), 7.15 (1H, d, J=4.4 Hz), 7.19-7.23 (1H, m, J=4.4 Hz), 7.61-7.63 (2H, m), 7.69-7.71 (1H, m), 7.92-7.95 (1H, m), 8.09-8.11 (1H, m), 8.13-8.14 (1H, m) 8.71 (1H, s) 8.82 (1H, d, J=4.4 Hz)
MS (ES) m/z=427 (MH+)
HPLC=84.2%

Example 21

N-butyl-N-{3-[3-(thiophene-2-carbonyl)-pyrazolo[1,5-a]pyrimidin-7-yl]-phenyl}-ethanesulfonamide $^1$H NMR (400 MHz, CDCl$_3$): δ 0.91 (3H, t, J=7.2 Hz), 1.36-1.44 (5H, m), 1.52-1.57 (2H, m), 3.1 (2H, c, J=7.6 Hz), 3.78 (2H, t, J=7.2 Hz), 7.16 (1H, d, J=4.4 Hz), 7.20-7.25 (1H, m), 7.61-7.63 (2H, m), 7.69-7.71 (1H, m), 7.99-8.02 (1H, m) 8.09-8.11 (2H, m) 8.71 (1H, s) 8.82 (1H, d, J=4.4 Hz)
MS (ES) m/z=469 (MH+)
HPLC=99.06%

Example 22

7-(3-(2-isothiazolidinyl-1,1-dioxide)-phenyl)-3-(thiophene-2-carbonyl)-pyrazolo[1,5-a]pyrimidine $^1$H NMR (400 MHz, CDCl$_3$): δ 2.57-2.61 (2H, m), 3.43 (2H, t, J=7.6 Hz), 3.87 (2H, t, J=6.4 Hz), 7.14 (1H, d, J=4 Hz), 7.19 (1H, t), 7.46-7.50 (1H, m), 7.58 (1H, t), 7.68-7.69 (1H, d, J=4 Hz), 7.78-7.79 (1H, d), 7.9 (1H, s) 8.09 (1H, d, J=3.2 Hz) 8.69 (1H, s) 8.79 (1H, d, J=4.4 Hz)
MS (ES) m/z=425 (MH+)
HPLC=97.1%

Example 23

N-methyl-N-{3-[3-(thiophene-2-carbonyl)-pyrazolo[1,5-a]pyrimidin-7-yl]-phenyl}-2-propane-sulfonamide $^1$H NMR (400 MHz, CDCl$_3$): δ 1.4 (6H, d, J=6.8 Hz), 3.36-3.41 (1H, m), 3.47 (3H, s), 7.15 (1H, d, J=4.4 Hz), 7.18-7.21 (1H, m), 7.58-7.64 (2H, m), 7.69-7.71 (1H, m), 7.89-7.93 (1H, m), 8.09-8.10 (1H, m), 8.14-8.16 (1H, m) 8.7 (1H, s) 8.81 (1H, d, J=4.4 Hz)
MS (ES) m/z=441 (MH+)
HPLC=96.35%

Example 24

N-ethyl-N-{3-[3-(thiophene-2-carbonyl)-pyrazolo[1,5-a]pyrimidin-7-yl]-phenyl}-2-propane-sulfonamide $^1$H NMR (400 MHz, CDCl$_3$): δ 1.21 (3H, t, J=6.8 Hz), 1.41 (6H, d, J=6.4 Hz), 3.28-3.32 (1H, m), 3.87 (2H, c, J=7.2 Hz), 7.16 (1H, d, J=4.4 Hz), 7.18-7.21 (1H, m), 7.61-7.62 (2H, m), 7.69-7.71 (1H, m), 7.9-8.1 (1H, m), 8.09-8.12 (1H, m) 8.7 (1H, s) 8.81 (1H, d, J=4.4 Hz).
MS (ES) m/z=455 (MH+)
HPLC=88.35%

Example 25

N-propyl-N-{3-[3-(thiophene-2-carbonyl)-pyrazolo[1,5-a]pyrimidin-7-yl]-phenyl}-2-propane-sulfonamide $^1$H NMR (400 MHz, CDCl$_3$): δ 0.93 (3H, t, J=7.2 Hz), 1.41 (6H, d, J=6.8 Hz), 1.57 (2H, q, J=7.2 Hz), 3.3 (1H, m, J=6.8 Hz), 3.77 (2H, t, J=7.2 Hz), 7.16 (1H, d, J=4.4 Hz), 7.19-7.21 (1H, m), 7.61-7.63 (2H, m), 7.69-7.71 (1H, m), 7.99-8.11 (1H, m), 8.09-8.13 (2H, m), 8.7 (1H, s), 8.81 (1H, d, J=4.4 Hz)
MS (ES) m/z=469 (MH+)
HPLC=97%

Example 26

N-butyl-N-{3-[3-(thiophene-2-carbonyl)-pyrazolo[1,5-a]pyrimidin-7-yl]-phenyl}-2-propane-sulfonamide $^1$H NMR (400 MHz, CDCl$_3$): δ 0.9 (3H, t, J=7.2 Hz), 1.36 (2H, q, J=8 Hz), 1.41 (6H, d, J=6.8 Hz), 1.51-1.55 (2H, m), 3.29 (1H, m, J=6.4 Hz), 8.81 (2H, t, J=6.8 Hz), 7.16 (1H, d, J=4.4 Hz), 7.19-7.21 (1H, m), 7.62-7.63 (2H, m), 7.70-7.71 (1H, m), 7.99-8.01 (1H, m), 8.10-8.14 (2H, m), 8.7 (1H, s), 8.82 (1H, d, J=4.4 Hz)

MS (ES) m/z=483 (MH+)
HPLC=100%

Example 27

N-[3-(3-cyano-pyrazolo[1,5-a]pyrimidin-7-yl)-phenyl]-N-2-propynyl-methanesulfonamide $^1$H NMR (400 MHz, CDCl$_3$): δ 2.53 (1, s), 3.1 (3H, s), 4.53 (2H, s), 7.19 (1H, d, J=4.4 Hz), 7.65 (1H, t, J=7.6 Hz), 7.85-7.88 (1H, m, J=4.4 Hz), 8.0-8.29 (1H, m), 8.27-8.28 (1H, m), 8.42 (1H, s), 8.79 (1H, d, J=4.4 Hz)
MS (ES) m/z=352 (MH$^+$)
HPLC=95.78%

Example 28

N-[3-(3-cyano-pyrazolo[1,5-a]pyrimidin-7-yl)-phenyl]-N-propyl-ethanesulfonamide $^1$H NMR (400 MHz, CDCl$_3$): δ 0.93 (3H, t, J=7.6 Hz), 1.41 (3H, t, J=7.2 Hz), 1.54-1.59 (2H, m), 3.01 (2H, q, J=7.2 Hz), 3.74 (2H, t, J=7.2 Hz), 7.2 (1H, d, J=4.4 Hz), 7.59-7.65 (2H, m), 7.96-7.99 (1H, m), 8.07-8.08 (1H, m), 8.41 (1H, s), 8.78 (1H, d, J=4.4 Hz)
MS (ES) m/z=370 (MH+)
HPLC=98%

Example 29

N-[3-(3-cyano-pyrazolo[1,5-a]pyrimidin-7-yl)-phenyl]-N-ethyl-ethanesulfonamide $^1$H NMR (400 MHz, CDCl$_3$): δ 1.21 (3H, t, J=7.2 Hz), 1.42 (3H, t, J=7.6 Hz), 3.09 (2H, q, J=7.6 Hz), 3.84 (2H, q, J=7.2 Hz), 7.2 (1H, d, J=4 Hz), 7.58-7.65 (2H, m), 7.97-7.99 (1H, m), 8.07 (1H, t, J=1.6 Hz), 8.42 (1H, s), 8.78 (1H, d, J=4.8 Hz)
MS (ES) m/z=356 (MH+)
HPLC=99%

Example 30

N-[3-(3-cyano-pyrazolo[1,5-a]pyrimidin-7-yl)-phenyl]-N-2-propynyl-propane-2-sulfonamide $^1$H NMR (400 MHz, CDCl$_3$): δ 1.43 (6H, d, J=7.2 Hz), 2.41-2.42 (1H, m), 3.43-3.50 (1H, m), 3.54 (2H, s), 7.2 (1H, d, J=4 Hz), 7.63 (1H, t, J=7.6 Hz), 7.77-7.80 (1H, m), 7.99-8.02 (1H, m), 8.21-8.22 (1H, m), 8.42 (1H, s) 8.78 (1H, d, J=4.4 Hz)
MS (ES) m/z=380 (MH+)
HPLC=97.46%

Example 31

N-[3-(3-cyano-pyrazolo[1,5-a]pyrimidin-7-yl)-phenyl]-N-methyl-ethanesulfonamide $^1$H NMR (400 MHz, CDCl$_3$): δ 1.4 (3H, t, J=7.2 Hz), 3.11 (2H, q, J=7.2 Hz), 3.43 (3H, s), 7.19 (1H, d, J=4.4 Hz), 7.60-7.63 (2H, m), 7.89-7.92 (1H, m), 8.11 (1H, a), 8.42 (1H, s), 8.78 (1H, d, J=4.4 Hz)

MS (ES) m/z=342 (MH+)
HPLC=91%

Example 32

N-[3-(3-cyano-pyrazolo[1,5-a]pyrimidin-7-yl)-phenyl]-N-butyl-ethanesulfonamide $^1$H NMR (400 MHz, CDCl$_3$): δ 1.43 (3H, t, J=7.2 Hz), 2.49 (1H, t, J=2.4 Hz), 3.26 (2H, q, J=7.2 Hz), 4.54 (2H, d, J=2.4 Hz), 7.2 (1H, d, J=4 Hz), 7.64 (1H, t, J=8 Hz), 7.82-7.85 (1H, m), 8.00-8.03 (1H, m), 8.25 (1H, t, J=2 Hz), 8.42 (1H, s), 8.79 (1H, d, J=4.4 Hz)
MS (ES) m/z=366 (MH+)
HPLC=98%

Example 33

7-(3-(2-isothiazolidinyl-1,1-dioxide)-phenyl)-3-cyano-pyrazolo[1,5-a]pyrimidine $^1$H NMR (400 MHz, DMSO-d$_6$): δ 2.47-2.51 (2H, m), 3.61 (2H, t, J=7.6 Hz), 3.87 (2H, t, J=6.8 Hz), 7.52-7.56 (1H, m), 7.6 (1H, d, J=4.8 Hz), 7.66 (1H, t), 7.8-7.85 (2H, m), 8.88 (1H, s), 8.95 (1H, d, J=4.4 Hz)
MS (ES) m/z=340 (MH+)
HPLC=91.47%

Example 34

N-[3-(3-cyano-pyrazolo[1,5-a]pyrimidin-7-yl)-phenyl]-N-methyl-2-propanesulfonamide $^1$H NMR (400 MHz, CDCl$_3$): δ 1.39 (6H, d, J=6.8 Hz), 3.38 (1H, m), 3.45 (3H, s), 7.19 (1H, d, J=4 Hz), 7.56-7.66 (2H, m), 7.87-7.90 (1H, m), 8.125 (1H, t, J=2 Hz), 8.41 (1H, s), 8.78 (1H, d, J=4 Hz)
MS (ES) m/z=356 (MH+)
HPLC=91%

Example 35

N-[3-(3-cyano-pyrazolo[1,5-a]pyrimidin-7-yl)-phenyl]-N-ethyl-2-propanesulfonamide $^1$H NMR (400 MHz, CDCl$_3$): δ 1.95 (3H, t, J=7.2 Hz), 1.41 (6H, d, J=6.8 Hz), 3.28 (1H, m), 3.86 (2H, q, J=7.2 Hz), 7.2 (1H, d, J=4.4 Hz), 7.61-7.62 (2H, m), 7.96-7.99 (1H, m), 8.08-8.09 (1H, m), 8.41 (1H, s), 8.78 (1H, d, J=4 Hz)
MS (ES) m/z=370 (MH+)
HPLC=98%

Example 36

N-[3-(3-cyano-pyrazolo[1,5-a]pyrimidin-7-yl)-phenyl]-N-butyl-2-propanesulfonamide $^1$H NMR (400 MHz, CDCl$_3$): δ 0.89 (3H, t, J=7.2 Hz), 1.32-1.36 (2H, m), 1.53-1.56 (6H, d, J=6.8 Hz), 1.49-1.51 (2H, m), 3.27 (1H, m), 3.79 (2H, t, J=7.6 Hz), 7.2 (1H, d, J=4.4 Hz), 7.61-7.63 (2H, m), 7.95-7.98 (1H, m), 8.1 (1H, a), 8.41 (1H, s), 8.78 (1H, d, J=4 Hz)

MS (ES) m/z=398 (MH+)
HPLC=95%

Example 37

N-[3-(3-cyano-pyrazolo[1,5-a]pyrimidin-7-yl)-phenyl]-N-propyl-2-propanesulfonamide ¹H NMR (400 MHz, CDCl₃): δ 0.92 (3H, t, J=7.2 Hz), 1.4 (6H, d, J=6.8 Hz), 1.53-1.56 (2H, m), 3.27 (1H, m), 3.76 (2H, t, J=7.6 Hz), 7.2 (1H, d, J=4.4 Hz), 7.61-7.63 (2H, m), 7.96-7.98 (1H, m), 8.1 (1H, a), 8.41 (1H, s), 8.78 (1H, d, J=4 Hz)
MS (ES) m/z=384 (MH+)
HPLC=98.05%

Example 38

N-[3-(3-cyano-pyrazolo[1,5-a]pyrimidin-7-yl)-phenyl]-N-2-propynyl-ethanesulfonamide ¹H NMR (400 MHz, CDCl₃): δ 7.2 (3H, t, J=7.6 Hz), 2.48 (1H, s), 3.25 (2H, c, J=7.2 Hz), 4.54 (2H, s), 7.2 (1H, d, J=4 Hz), 7.64 (1H, t, J=8.4 Hz), 7.82-7.85 (1H, m), 7.99-8.03 (1H, m), 8.26-8.26 (1H, m), 8.42 (1H, s) 8.79 (1H, d, J=4.1 Hz)
MS (ES) m/z=366 (MH+)
HPLC=97.7%

Example 39

N-methyl-N-{3-[3-(pyridin-2-carbonyl)-pyrazolo[1,5-a]pyrimidin-7-yl]-phenyl}-methanesulfonamide ¹H NMR (400 MHz, CDCl₃): δ 2.92 (3H, s), 3.41 (3H, s), 7.17 (1H, d, J=4.4 Hz), 7.48-7.51 (1H, m), 7.62-7.63 (2H, m), 7.90-7.94 (2H, m), 8.16-8.16 (1H, m), 8.24 (1H, d, J=6.8 Hz), 8.73-8.75 (1H, m), 8.90 (1H, d, J=4.4 Hz), 9.36 (1H, s)
MS (ES) m/z=408 (MH+)
HPLC=99%

Example 40

N-ethyl-N-{3-[3-(pyridin-2-carbonyl)-pyrazolo[1,5-a]pyrimidin-7-yl]-phenyl}-methanesulfonamide ¹H NMR (400 MHz, CDCl₃): δ 1.22 (3H, t, J=7.2 Hz), 2.97 (3H, s), 3.82 (2H, q, J=7.2 Hz), 7.18 (1H, d, J=4 Hz), 7.48-7.51 (1H, m), 7.59-7.67 (2H, m), 7.90-7.94 (1H, m), 7.98-8.00 (1H, m), 8.15 (1H, s), 8.24 (1H, d, J=7.6 Hz), 8.75 (1H, d, J=4.8 Hz), 8.9 (1H, d, J=4.4 Hz), 9.36 (1H, s)
MS (ES) m/z=422 (MH+)
HPLC=100%

Example 41

N-2-propynyl-N-{3-[3-(pyridin-2-carbonyl)-pyrazolo[1,5-a]pyrimidin-7-yl]-phenyl}-methanesulfonamide ¹H NMR (400 MHz, CDCl₃): δ 2.52-2.53 (1H, m), 3.12 (3H, s), 4.53-4.54 (2H, m), 7.17 (1H, d, J=4.4 Hz), 7.48-7.52 (1H, m), 7.65 (2H, t, J=8 Hz), 7.82-7.85 (1H, m), 7.92 (1H, t, J=0.8 Hz), 8.03-8.06 (1H, m), 8.24 (1H, d, J=8.4 Hz), 8.35 (1H, s), 8.75 (1H, d, J=5.6 Hz), 8.9 (1H, d, J=5.6 Hz), 9.37 (1H, s)
MS (ES) m/z=432 (MH+)
HPLC=96%

Example 42

N-methyl-N-{3-[3-(pyridin-2-carbonyl)-pyrazolo[1,5-a]pyrimidin-7-yl]-phenyl}-ethanesulfonamide ¹H NMR (400 MHz, CDCl₃): δ 1.4 (3H, t, J=7.6 Hz), 3.12 (2H, q, J=7.6 Hz), 3.44 (3H, s), 7.17 (1H, d, J=4.4 Hz), 7.48-7.51 (1H, m), 7.61-7.64 (2H, m), 7.88-7.93 (2H, m), 8.16 (1H, t, J=2 Hz), 8.24 (1H, d, J=8.4 Hz), 8.74-8.75 (1H, m), 8.89 (1H, d, J=5.2 Hz), 9.36 (1H, s)
MS (ES) m/z=422 (MH+)
HPLC=100%

Example 43

N-ethyl-N-{3-[3-(pyridin-2-carbonyl)-pyrazolo[1,5-a]pyrimidin-7-yl]-phenyl}-ethanesulfonamide ¹H NMR (400 MHz, CDCl₃): δ 1.35 (3H, t, J=7.2 Hz), 1.33 (3H, t, J=7.2 Hz), 3.05 (2H, q, J=7.2 Hz), 3.77 (2H, q, J=7.2 Hz), 7.14 (1H, d, J=4.8 Hz), 7.40-7.43 (1H, m), 7.54-7.56 (2H, m), 7.82-7.85 (1H, m), 7.92-7.93 (1H, m), 8.1 (1H, s), 8.13 (1H, d, J=8 Hz), 8.66 (1H, d, J=4.4 Hz), 8.81 (1H, d, J=4.4 Hz), 9.28 (1H, s)
MS (ES) m/z=436 (MH+)
HPLC=95%

Example 44

N-2-propynyl-N-{3-[3-(pyridin-2-carbonyl)-pyrazolo[1,5-a]pyrimidin-7-yl]-phenyl}-ethanesulfonamide ¹H NMR (400 MHz, CDCl₃): δ 1.42 (3H, t, J=7.2 Hz), 2.47 (1H), 3.26 (2H, q, J=7.2 Hz), 4.54 (2H, d, J=2.4 Hz), 7.17 (1H, d, J=4.8 Hz), 7.48-7.51 (1H, m), 7.63 (1H, t, J=7.6 Hz, 7.8-7.82 (1H, m), 7.89-7.93 (1H, m), 8.02-8.05 (1H, m), 8.23 (1H, d, J=8 Hz), 8.3 (1H, t, J=2 Hz), 8.73-8.75 (1H, m), 8.89 (1H, d, J=5.2 Hz), 9.36 (1H, s)
MS (ES) m/z=446 (MH+)
HPLC=98%

Example 45

N-methyl-N-{3-[3-(pyridin-4-carbonyl)-pyrazolo[1,5-a]pyrimidin-7-yl]-phenyl}-methanesulfonamide ¹H NMR (400 MHz, CDCl₃): δ 2.92 (3H, s), 3.41 (3H, s), 7.2 (1H, d, J=4.4 Hz), 7.26-7.64 (2H, m), 7.71-7.73 (2H, m), 7.93-7.96 (1H, m), 8.127-8.129 (1H, m), 8.57 (1H, s), 8.81-8.83 (3H, m)
MS (ES) m/z=408 (MH+)
HPLC=95%

Example 46

N-ethyl-N-{3-[3-(pyridin-4-carbonyl)-pyrazolo[1,5-a]pyrimidin-7-yl]-phenyl}-methanesulfonamide ¹H NMR (400 MHz, CDCl₃): δ 1.22 (3H, t, J=7.2 Hz), 2.96 (3H, s), 3.82 (2H, q, J=7.2 Hz), 7.22 (1H, d, J=4.4 Hz), (1H, m), 5.73 (2H, d, J=5.6 Hz), 8.01 (1H, d, J=7.6 Hz), 8.1 (1H, t, J=2 Hz), 8.57 (1H, s), 8.82-8.84 (3H, m)

MS (ES) m/z=422 (MH+)
HPLC=89%

Example 47

N-methyl-N-{3-[3-(pyridin-4-carbonyl)-pyrazolo[1,5-a]pyrimidin-7-yl]-phenyl}-ethanesulfonamide $^1$H NMR (400 MHz, CDCl$_3$): δ 1.39 (3H, t, J=7.2 Hz), 3.11 (2H, q, J=7.2 Hz), 3.44 (3H, s), 7.2 (1H, d, J=4.8 Hz), 7.62-7.63 (2H, m), 7.71-7.72 (2H, m), 7.92-7.94 (1H, m), 8.13-8.14 (1H, m), 8.57 (1H, s), 8.81-8.83 (3H, m)
MS (ES) m/z=422 (MH+)
HPLC=94%

Example 48

N-ethyl-N-{3-[3-(pyridin-4-carbonyl)-pyrazolo[1,5-a]pyrimidin-7-yl]-phenyl}-ethanesulfonamide $^1$H NMR (400 MHz, CDCl$_3$); δ 1.13 (3H, t, J=7.2 Hz), 1.318 (3H, t, J=7.2 Hz), 3.04 (2H, q, J=7.2 Hz), 3.77 (2H, q, J=7.2 Hz), 7.18 (1H, d, J=4.8 Hz), 7.52-7.58 (2H, m), 7.61-7.94 (2H, m), 8.05 (1H, s), 8.47 (1H, s), 8.71-8.73 (3H, m)
MS (ES) m/z=436 (MH+)
HPLC=89%

Example 49

N-2-propynyl-N-{3-[3-(pyridin-4-carbonyl)-pyrazolo[1,5-a]pyrimidin-7-yl]-phenyl}-ethanesulfonamide $^1$H NMR (400 MHz, CDCl$_3$): δ 1.22 (3H, t, J=7.2 Hz), 2.96 (3H, s), 3.82 (2H, q, J=7.2 Hz), 7.22 (1H, d, J=4.4 Hz), 7.58-7.60 (1H, m), 7.66 (1H, t, J=8 Hz), 7.71-7.73 (2H, m), 8.01 (1H, d, J=7.6 Hz), 8.1 (1H, t, J=2 Hz), 8.57 (1H, s), 8.82-8.84 (3H, m)
MS (ES) m/z=422 (MH+)
HPLC=89%

Example 50

N-2-propynyl-N-{3-[3-(pyridin-4-carbonyl)-pyrazolo[1,5-a]pyrimidin-7-yl]-phenyl}-methanesulfonamide $^1$H NMR (400 MHz, CDCl$_3$): δ 2.53 (1H, t, J=2 Hz), 3.11 (3H, s), 4.54 (2H, d, J=2.4 Hz), 7.2 (1H, d, J=4.4 Hz), 7.66 (1H, t, J=7.6 Hz), 7.72-7.73 (2H, m), 7.86-7.89 (1H, m), 8.03-8.05 (1H, m), 8.31 (1H, t, J=2 Hz), 8.56 (1H, s), 8.82-8.84 (3H, m)
MS (ES) m/z=432 (MH+)
HPLC=93%

Example 51

N-methyl-N-{3-[3-(fluorobenzene-4-carbonyl)-pyrazolo[1,5-a]pyrimidin-7-yl]-phenyl}-methanesulfonamide $^1$H NMR (400 MHz, CDCl$_3$): δ 2.93 (3H, s), 3.42 (3H, s), 7.15-7.20 (3H, m), 7.61-7.63 (2H, m), 7.94-7.99 (3H, m), 8.12-8.13 (1H, m), 8.55 (1H, s), 8.78 (1H, d, J=4.4 Hz)
MS (ES) m/z=425 (MH+)
HPLC=98%

Example 52

N-ethyl-N-{3-[3-(fluorobenzene-4-carbonyl)-pyrazolo[1,5-a]pyrimidin-7-yl]-phenyl}-methanesulfonamide $^1$H NMR (400 MHz, CDCl$_3$): δ 1.23 (3H, t, J=7.2 Hz), 2.97 (3H, s), 3.82 (2H, q, J=7.2 Hz), 7.16-7.20 (3H, m), 7.56-7.60 (1H, m), 7.65 (1H, t, J=8 Hz), 7.96-8.02 (3H, m), 8.1 (1H, t, J=2 Hz), 8.55 (1H, s), 8.79 (1H, d, J=4.4 Hz)
MS (ES) m/z=439 (MH+)
HPLC=98%

Example 53

N-methyl-N-{3-[3-(fluorobenzene-4-carbonyl)-pyrazolo[1,5-a]pyrimidin-7-yl]-phenyl}-ethanesulfonamide $^1$H NMR (400 MHz, CDCl$_3$): δ 1.38 (3H, t, J=7.2 Hz), 3.11 (2H, q, J=7.2 Hz), 3.42 (3H, s), 7.13-7.17 (3H, m), 7.59-7.61 (2H, m), 7.90-7.97 (3H, m, J=8 Hz), 8.13 (1H, a), 8.53 (1H, s), 8.76 (1H, d, J=4.4 Hz)
MS (ES) m/z=439 (MH+)
HPLC=94%

Example 54

N-ethyl-N-{3-[3-(fluorobenzene-4-carbonyl)-pyrazolo[1,5-a]pyrimidin-7-yl]-phenyl}-ethanesulfonamide $^1$H NMR (400 MHz, CDCl$_3$): δ 1.21 (3H, t, J=7.2 Hz), 1.41 (3H, t, J=7.2 Hz), 3.1 (2H, q, J=7.2 Hz), 3.84 (2H, q, J=7.2 Hz), 7.14-7.18 (3H, m), 7.58 (2H, m), 7.94-8.01 (3H, m), 8.1 (1H, a), 8.54 (1H, s), 8.77 (1H, d, J=4.4 Hz)
MS (ES) m/z=453 (MH+)
HPLC=99%

Example 55

N-2-propynyl-N-{3-[3-(fluorobenzene-4-carbonyl)-pyrazolo[1,5-a]pyrimidin-7-yl]-phenyl}-ethanesulfonamide $^1$H NMR (400 MHz, CDCl$_3$): δ 1.43 (3H, t, J=7.2 Hz), 2.48 (1H, t, J=2.4 Hz), 3.27 (2H, q, J=7.2 Hz), 4.54 (2H, d, J=2.4 Hz), 7.15-7.2 (3H, m), 7.64 (1H, t, J=8 Hz), 7.81-7.84 (1H, m), 7.96-8.04 (3H, m), 8.28 (1H, a), 8.56 (1H, s), 8.79 (1H, d, J=4.4 Hz)
MS (ES) m/z=463 (MH+)
HPLC=96%

Example 56

N-2-propynyl-N-{3-[3-(fluorobenzene-4-carbonyl)-pyrazolo[1,5-a]pyrimidin-7-yl]-phenyl}-methanesulfonamide $^1$H NMR (400 MHz, CDCl$_3$): δ 2.54 (1H, t, J=2 Hz), 3.1 (3H, s), 4.52 (2H, d, J=2 Hz), 7.14-7.18 (3H, m), 7.64 (1H, t, J=7.6 Hz), 7.83-7.86 (1H, m), 7.94-7.96 (2H, m), 8.02-8.04 (1H, m), 8.3 (1H, t, J=2 Hz), 8.54 (1H, s), 8.77 (1H, d, J=4 Hz)

MS (ES) m/z=449 (MH+)
HPLC=96%

Example 57

N-methyl-N-{3-[3-(4-methoxybenzoyl)-pyrazolo[1,5-a]pyrimidin-7-yl]-phenyl}-methanesulfonamide $^1$H NMR (400 MHz, CDCl$_3$): δ 2.93 (3H, s), 3.42 (3H, s), 3.9 (3H, s), 6.97-7.01 (2H, m), 7.12 (1H, d, J=4.4 Hz), 7.61-7.65 (2H, m), 7.94-7.99 (3H, m), 8.13 (1H, a), 8.55 (1H, s), 8.78 (1H, d, J=3.6 Hz)
MS (ES) m/z=437 (MH+)
HPLC=99%

Example 58

N-ethyl-N-{3-[3-(4-methoxybenzoyl)-pyrazolo[1,5-a]pyrimidin-7-yl]-phenyl}-methanesulfonamide $^1$H NMR (400 MHz, CDCl$_3$): δ 1.23 (3H, t, J=7.2 Hz), 2.97 (3H, s), 3.82 (2H, q, J=7.2 Hz), 3.9 (3H, s), 6.98-7.00 (2H, m), 7.14 (1H, d, J=4 Hz), 7.59-7.60 (1H, m), 7.65 (1H, t, J=8 Hz), 7.96-8.03 (3H, m), 8.1 (1H, t, J=2 Hz) 8.55 (1H, s), 8.78 (1H, d, J=4 Hz)
MS (ES) m/z=451 (MH+)
HPLC=98%

Example 59

N-methyl-N-{3-[3-(4-methoxybenzoyl)-pyrazolo[1,5-a]pyrimidin-7-yl]-phenyl}-ethane-sulfonamide $^1$H NMR (400 MHz, CDCl$_3$): δ 1.41 (3H, t, J=7.2 Hz), 3.13 (2H, q, J=7.2 Hz), 3.45 (3H, s), 3.9 (3H, s), 6.98-7.00 (2H, m), 7.12 (1H, d, J=4.4 Hz), 7.61-7.63 (2H, m), 7.93-7.98 (3H, m), 8.14 (1H, t, J=1.2 Hz), 8.55 (1H, s), 8.78 (1H, d, J=4 Hz)
MS (ES) m/z=451 (MH+)
HPLC=97%

Example 60

N-ethyl-N-{3-[3-(4-methoxybenzoyl)-pyrazolo[1,5-a]pyrimidin-7-yl]-phenyl}-ethanesulfonamide $^1$H NMR (400 MHz, CDCl$_3$): δ 1.23 (3H, t, J=7.2 Hz), 1.43 (3H, t, J=7.2 Hz), 3.12 (2H, q, J=7.2 Hz), 3.86 (2H, q, J=7.2 Hz), 3.91 (3H, s), 6.98-7.00 (2H, m), 7.14 (1H, d, J=4 Hz), 7.6-7.65 (2H, m), 7.96-8.02 (3H, m), 8.11 (1H, t, J=1.6 Hz), 8.55 (1H, s), 8.78 (1H, d, J=4 Hz)
MS (ES) m/z=465 (MH+)
HPLC=98%

Example 61

N-2-propynyl-N-{3-[3-(4-methoxybenzoyl)-pyrazolo[1,5-a]pyrimidin-7-yl]-phenyl}-ethanesulfonamide $^1$H NMR (400 MHz, CDCl$_3$): δ 1.43 (3H, t, J=7.2 Hz), 2.48 (1H, t, J=2.4 Hz), 3.27 (2H, q, J=7.2 Hz), 3.9 (3H, s), 4.55 (2H, d, J=2.4 Hz), 6.98-7.00 (2H, m), 7.13 (1H, d, J=4.4 Hz), 7.64 (1H, t, J=8 Hz), 7.80-7.83 (1H, m), 7.96-7.98 (2H, m) 8.03-8.05 (1H, m), 8.28 (1H, a), 8.55 (1H, s), 8.78 (1H, d, J=3.6 Hz)

MS (ES) m/z=475 (MH+)
HPLC=97%

Example 62

N-2-propynyl-N-{3-[3-(4-methoxybenzoyl)-pyrazolo[1,5-a]pyrimidin-7-yl]-phenyl}-methanesulfonamide $^1$H NMR (400 MHz, CDCl$_3$): δ 2.53 (1H, t, J=2 Hz), 3.11 (3H, s), 3.87 (3H, s), 4.53 (2H, d, J=2 Hz), 6.98 (2H, d, J=8.8 Hz), 7.12 (1H, d, J=4.4 Hz), 7.63 (1H, t, J=7.6 Hz), 7.82-7.84 (1H, m), 7.95 (2H, d, J=8.8 Hz), 8.03 (1H, d, J=7.6 Hz), 8.31 (1H, t, J=2 Hz), 8.54 (1H, s), 8.76 (1H, d, J=4.4 Hz)
MS (ES) m/z=461 (MH+)
HPLC=100%

Example 63

N-methyl-N-{3-[3-(4-methylbenzoyl)-pyrazolo[1,5-a]pyrimidin-7-yl]-phenyl}-methanesulfonamide $^1$H NMR (400 MHz, CDCl$_3$): δ 2.5 (3H, s), 2.97 (3H, s), 3.46 (3H, s), 7.18 (1H, d, J=4.4 Hz), 7.34 (2H, d, J=8.4 Hz), 7.65-7.67 (2H, m), 7.89 (2H, d, J=8 Hz), 7.98-8.00 (1H, m), 8.17 (1H, s), 8.58 (1H, s), 8.83 (1H, d, J=4.4 Hz)
MS (ES) m/z=421 (MH$^+$)
HPLC=99%

Example 64

N-ethyl-N-{3-[3-(4-methylbenzoyl)-pyrazolo[1,5-a]pyrimidin-7-yl]-phenyl}-methanesulfonamide $^1$H NMR (400 MHz, CDCl$_3$): δ 1.23 (3H, t, J=7.2 Hz), 2.45 (3H, s), 2.96 (3H, s), 3.82 (2H, q, J=7.2 Hz), 7.15 (1H, d, J=4.4 Hz), 7.29-7.3 (2H, m), 7.58-7.64 (2H, m), 7.83-7.85 (2H, m), 7.99-8.02 (1H, m), 8.1 (1H, t, J=2 Hz), 8.53 (1H, s), 8.79 (1H, d, J=4.8 Hz)
MS (ES) m/z=435 (MH$^+$)
HPLC=96%

Example 65

N-methyl-N-{3-[3-(4-methylbenzoyl)-pyrazolo[1,5-a]pyrimidin-7-yl]-phenyl}-ethanesulfonamide $^1$H NMR (400 MHz, CDCl$_3$): δ 1.41 (3H, t, J=7.2 Hz), 2.46 (3H, s), 3.12 (2H, q, J=7.2 Hz), 3.44 (3H, s), 7.13 (1H, d, J=4 Hz), 7.31 (2H, d, J=8.4 Hz), 7.61-7.63 (2H, m), 7.85-7.87 (2H, m), 7.92-7.93 (1H, m), 8.13-8.14 (1H, m), 8.54 (1H, s), 8.79 (1H, d, J=4.4 Hz)
MS (ES) m/z=435 (MH+)
HPLC=98%

Example 66

N-ethyl-N-{3-[3-(4-methylbenzoyl)-pyrazolo[1,5-a]pyrimidin-7-yl]-phenyl}-ethanesulfonamide $^1$H NMR (400 MHz, CDCl$_3$): δ 1.22 (3H, t, J=7.2 Hz), 1.42 (3H, t, J=7.2 Hz), 2.46 (3H, s), 3.11 (2H, q, J=7.2 Hz), 3.85 (2H, q, J=7.2 Hz), 7.15 (1H, d, J=4.4 Hz), 7.31 (2H, d, J=8.2 Hz), 7.60-7.66 (2H, m), 7.84-7.86 (2H, m), 8 (1H, d, J=7.6 Hz), 8.11 (1H, t, J=1.6 Hz), 8.54 (1H, s), 8.8 (1H, d, J=4.4 Hz)
MS (ES) m/z=449 (MH+)
HPLC=100%

Example 67

N-2-propynyl-N-{3-[3-(4-methylbenzoyl)-pyrazolo[1,5-a]pyrimidin-7-yl]-phenyl}-ethanesulfonamide $^1$H NMR (400 MHz, CDCl$_3$): δ 1.43 (3H, t, J=7.2 Hz), 2.46 (3H, s), 2.48 (1H, t, J=2.4 Hz), 3.27 (2H, q, J=7.2 Hz), 4.54 (2H, d, J=2.4 Hz), 7.14 (1H, d, J=4 Hz), 7.31 (2H, d, J=8 Hz), 7.63 (1H, t, J=8 Hz), 7.81-7.86 (3H, m), 8.03 (1H, d, J=8 Hz), 8.28 (1H, t, J=2 Hz), 8.54 (1H, s), 8.8 (1H, d, J=4.4 Hz)
MS (ES) m/z=459 (MH+)
HPLC=98%

Example 68

N-2-propynyl-N-{3-[3-(4-methylbenzoyl)-pyrazolo[1,5-a]pyrimidin-7-yl]-phenyl}-methanesulfonamide $^1$H NMR (400 MHz, CDCl$_3$): δ 2.46 (3H, s), 2.53 (1H, t, J=2.4 Hz), 3.11 (3H, s), 4.54 (2H, d, J=2.4 Hz), 7.14 (1H, d, J=4 Hz), 7.3 (2H, d, J=8 Hz), 7.64 (1H, t, J=8 Hz), 7.83-7.86 (3H, m), 8.03-8.05 (1H, m), 8.31 (1H, t, J=2 Hz), 8.54 (1H, s), 8.8 (1H, d, J=4.4 Hz)
MS (ES) m/z=445 (MH+)
HPLC=98%

Example 69

N-methyl-N-{3-[3-(benzoyl)-pyrazolo[1,5-a]pyrimidin-7-yl]-phenyl}-methanesulfonamide $^1$H NMR (400 MHz, CDCl$_3$): δ 2.93 (3H, s), 3.42 (3H, s), 7.15 (1H, d, J=4.4 Hz), 7.49-7.52 (2H, m), 7.58-7.63 (3H, m), 7.92-7.94 (3H, m), 8.13 (1H, a), 8.54 (1H, s), 8.81 (1H, d, J=4.4 Hz)
MS (ES) m/z=407 (MH+)
HPLC=96%

Example 70

N-ethyl-N-{3-[3-(benzoyl)-pyrazolo[1,5-a]pyrimidin-7-yl]-phenyl}-methanesulfonamide $^1$H NMR (400 MHz, CDCl$_3$): δ 1.22 (3H, t, J=7.2 Hz), 2.97 (3H, s), 3.82 (2H, q, J=7.2 Hz), 7.17 (1H, d, J=4.4 Hz), 7.49-7.52 (2H, m), 7.56-7.67 (3H, m), 7.91-7.94 (2H, m), 7.80-8.02 (1H, m), 8.11 (1H, t, J=2 Hz), 8.53 (1H, s), 8.82 (1H, d, J=4.4 Hz)
MS (ES) m/z=421 (MH+)
HPLC=98%

Example 71

N-methyl-N-{3-[3-(benzoyl)-pyrazolo[1,5-a]pyrimidin-7-yl]-phenyl}-ethanesulfonamide $^1$H NMR (400 MHz, CDCl$_3$): δ 1.39 (3H, t, J=7.2 Hz), 3.11 (2H, q, J=7.2 Hz), 3.43 (3H, s), 7.15 (1H, a), 7.47-7.61 (5H, m), 7.91 (3H, d, J=7.6 Hz), 8.14 (1H, s), 8.52 (1H, s), 8.79 (1H, a)
MS (ES) m/z=421 (MH+)
HPLC=98%

Example 72

N-ethyl-N-{3-[3-(benzoyl)-pyrazolo[1,5-a]pyrimidin-7-yl]-phenyl}-ethanesulfonamide $^1$H NMR (400 MHz, CDCl$_3$): δ 1.23 (3H, t, J=7.2 Hz), 1.42 (3H, t, J=7.2 Hz), 1.56 (3H, s), 3.11 (2H, q, J=7.2 Hz), 3.85 (2H, q, J=7.2 Hz), 7.17 (1H, d, J=4.4 Hz), 7.49-7.53 (2H, m), 7.58-7.66 (3H, m), 7.92-7.94 (2H, m), 8.01 (1H, d, J=7.6 Hz), 8.11 (1H, t, J=1.6 Hz), 8.54 (1H, s), 8.82 (1H, d, J=4.8 Hz)
MS (ES) m/z=435 (MH+)
HPLC=100%

Example 73

N-2-propynyl-N-{3-[3-(benzoyl)-pyrazolo[1,5-a]pyrimidin-7-yl]-phenyl}-ethanesulfonamide $^1$H NMR (400 MHz, CDCl$_3$): δ 1.43 (3H, t, J=7.2 Hz), 2.48 (1H, t, J=2.8 Hz), 3.27 (2H, q, J=7.2 Hz), 4.54 (2H, d, J=2.8 Hz), 7.16 (1H, d, J=4.4 Hz), 7.49-7.52 (2H, m), 7.58-7.66 (2H, m), 7.82 (1H, d, J=8 Hz), 7.93 (2H, d, J=6.8 Hz), 8.04 (1H, d, J=8 Hz), 8.29 (1H, a), 8.54 (1H, s), 8.81 (1H, d, J=4.4 Hz)
MS (ES) m/z=445 (MH+)
HPLC=97%

Example 74

N-2-propynyl-N-{3-[3-(benzoyl)-pyrazolo[1,5-a]pyrimidin-7-yl]-phenyl}-methanesulfonamide $^1$H NMR (400 MHz, CDCl$_3$): δ 2.53 (1H, t, J=2.4 Hz), 3.12 (3H, s), 4.54 (2H, d, J=2.4 Hz), 7.16 (1H, d, J=4.8 Hz), 7.49-7.53 (2H, m), 7.58-7.60 (1H, m), 7.65 (1H, t, J=8 Hz), 7.84-7.86 (1H, m), 7.92-7.94 (2H, m), 8.04 (1H, d, J=8 Hz), 8.32 (1H, t, J=2 Hz), 8.54 (1H, s), 8.82 (1H, d, J=4.4 Hz)
MS (ES) m/z=431 (MH+)
HPLC=97%

Example 75

N-methyl-N-{3-[3-(thiophene-2-carbonyl)-pyrazolo[1,5-a]pyrimidin-7-yl]-phenyl}-2-phenylethene-sulfonamide $^1$H NMR (400 MHz, CDCl$_3$): δ 3.35 (3H, s), 6.78 (1H, d, J=15.5 Hz), 7.13 (1H, d, J=4.6 Hz), 7.21 (1H, dd), 7.48-7.52 (6H, m), 7.6-7.63 (2H, m), 7.71 (1H, dd), 7.92-7.96 (1H, m), 8.06 (1H, dd), 8.13 (1H, m) 8.53 (1H, m) 8.8 (1H, d, J=4.6 Hz)
MS (ES) m/z=501 (MH+)
HPLC=96.98%

Example 76

N-methyl-N-{3-[3-(thiophene-2-carbonyl)-pyrazolo[1,5-a]pyrimidin-7-yl]-phenyl}-2,2,2-trifluoroethane-sulfonamide $^1$H NMR (400 MHz, CDCl$_3$): δ 3.48 (3H, s), 3.87 (2H, c, J=9.1 Hz), 7.16 (1H, d, J=4.6 Hz), 7.21 (1H, dd), 7.65-7.67 (1H, m), 7.68 (1H, s), 7.72 (1H, dd), 7.98-8.02 (1H, m), 8.09 (1H, dd), 8.2 (1H, m) 8.7 (1H, s) 8.84 (1H, d, J=4.6 Hz)
MS (ES) m/z=481 (MH+)
HPLC=99.05%

Example 77

N-methyl-N-{3-[3-(thiophene-2-carbonyl)-pyrazolo[1,5-a]pyrimidin-7-yl]-phenyl}-2-chlorobenzene-sulfonamide $^1$H NMR (400 MHz, CDCl$_3$): δ 3.47 (3H, s), 7.06 (1H, d, J=4.6 Hz), 7.19-7.23 (1H, m), 7.32-7.39 (1H, m), 7.46-7.57

(4H, m), 7.7-7.72 (1H, m), 7.92-8 (3H, m), 8.09-8.11 (1H, m), 8.67 (1H, s), 8.8 (1H, d, J=4.6 Hz)

MS (ES) m/z=510 (MH+)
HPLC=99.81%

Example 78

N-methyl-N-{3-[3-(thiophene-2-carbonyl)-pyrazolo[1,5-a]pyrimidin-7-yl]-phenyl}-3-chlorobenzene-sulfonamide $^1$H NMR (400 MHz, CDCl$_3$): δ 3.27 (3H, s), 7.11 (1H, d, J=4.6 Hz), 7.19-7.61 (7H, m), 7.7-7.72 (1H, m), 7.85 (1H, m), 7.97-8.01 (1H, m), 8.09-8.11 (1H, m), 8.68 (1H, s), 8.81 (1H, d, J=4.6 Hz)

MS (ES) m/z=510 (MH+)
HPLC=97.44%

Example 79

N-methyl-N-{3-[3-(thiophene-2-carbonyl)-pyrazolo[1,5-a]pyrimidin-7-yl]-phenyl}-4-chlorobenzene-sulfonamide $^1$H NMR (400 MHz, CDCl$_3$): δ 3.25 (3H, s), 7.1 (1H, d, J=4.6 Hz), 7.2-7.24 (1H, m), 7.33-7.37 (1H, m), 7.46-7.6 (5H, m), 7.72 (1H, dd), 7.85-7.87 (1H, m), 7.95-8 (1H, m), 8.09-8.11 (1H, m), 8.69 (1H, s) 8.82 (1H, d, J=4.6 Hz)

MS (ES) m/z=510 (MH+)
HPLC=99.69%

Example 80

N-methyl-N-{3-[3-(thiophene-2-carbonyl)-pyrazolo[1,5-a]pyrimidin-7-yl]-phenyl}-2,4-dichlorobenzene-sulfonamide $^1$H NMR (400 MHz, CDCl$_3$): δ 3.46 (3H, s), 7.08 (1H, d, J=4.6 Hz), 7.21 (1H, dd), 7.33 (1H, dd), 7.46-7.59 (3H, m), 7.71 (1H, dd), 7.87-7.98 (3H, m), 8.09 (1H, dd), 8.67 (1H, s), 8.81 (1H, d, J=4.6 Hz)

MS (ES) m/z=543 (MH+)
HPLC=98.04%

Example 81

N-methyl-N-{3-[3-(thiophene-2-carbonyl)-pyrazolo[1,5-a]pyrimidin-7-yl]-phenyl}-3,4-dichlorobenzene-sulfonamide $^1$H NMR (400 MHz, CDCl$_3$): δ 3.27 (3H, s), 7.11 (1H, d, J=4.6 Hz), 7.21 (1H, dd), 7.37-7.47 (2H, m), 7.56-7.62 (2H, m), 7.7-7.72 (2H, m), 7.86-7.88 (1H, m), 7.94-7.99 (1H, m), 8.09 (1H, dd), 8.67 (1H, s) 8.81 (1H, d, J=4.6 Hz)

MS (ES) m/z=543 (MH+)
HPLC=98.03%

Example 82

N-methyl-N-{3-[3-(thiophene-2-carbonyl)-pyrazolo[1,5-a]pyrimidin-7-yl]-phenyl}-2-cyanobenzene-sulfonamide $^1$H NMR (400 MHz, CDCl$_3$): δ 3.41 (3H, s), 7.15 (1H, d, J=4.6 Hz), 7.2 (1H, dd), 7.34-7.39 (1H, m), 7.53-7.59 (1H, m), 7.69-7.77 (3H, m), 7.83-7.87 (1H, m), 7.91-8.01 (3H, m), 8.1 (1H, dd), 8.63 (1H, s) 8.79 (1H, d, J=4.6 Hz)

MS (ES) m/z=500 (MH+)
HPLC=99.32%

Example 83

N-methyl-N-{3-[3-(thiophene-2-carbonyl)-pyrazolo[1,5-a]pyrimidin-7-yl]-phenyl}-3-cyanobenzene-sulfonamide $^1$H NMR (400 MHz, CDCl$_3$): δ 3.28 (3H, s), 7.13 (1H, d, J=4.6 Hz), 7.19-7.22 (1H, m), 7.33-7.36 (1H, m), 7.56-7.72 (3H, m), 7.83-7.97 (5H, m), 8.09 (1H, d, J=3.6 Hz), 8.66 (1H, s), 8.81 (1H, d, J=4.6 Hz)

MS (ES) m/z=500 (MH+)
HPLC=96.69%

Example 84

N-methyl-N-{3-[3-(thiophene-2-carbonyl)-pyrazolo[1,5-a]pyrimidin-7-yl]-phenyl}-4-cyanobenzene-sulfonamide $^1$H NMR (400 MHz, CDCl$_3$): δ 3.28 (3H, s), 7.12 (1H, d, J=4.2 Hz), 7.2-7.32 (3H, m), 7.58 (1H, t, J=8 Hz), 7.71-7.83 (4H, m), 7.91 (1H, a), 7.99 (1H, d, J=7.6 Hz), 8.09 (1H, d, J=3.3 Hz), 8.68 (1H, s), 8.83 (1H, d, J=3.9 Hz)

MS (ES) m/z=500 (MH+)
HPLC=97.9%

Example 85

N-methyl-N-{3-[3-(thiophene-2-carbonyl)-pyrazolo[1,5-a]pyrimidin-7-yl]-phenyl}-3-nitrobenzene-sulfonamide $^1$H NMR (400 MHz, CDCl$_3$): δ 3.3 (3H, s), 7.12 (1H, d, J=4.6 Hz), 7.22 (1H, dd), 7.38-7.43 (1H, m), 7.6 (1H, t, J=7.9 Hz), 7.7-7.77 (2H, m), 7.86-7.97 (3H, m), 8.09 (1H, dd), 8.4-8.5 (2H, m), 8.6 (1H, s) 8.8 (1H, d, J=4.6 Hz)

MS (ES) m/z=520 (MH+)
HPLC=99.14%

Example 86

N-methyl-N-{3-[3-(thiophene-2-carbonyl)-pyrazolo[1,5-a]pyrimidin-7-yl]-phenyl}-4-nitrobenzene-sulfonamide $^1$H NMR (400 MHz, CDCl$_3$): δ 3.3 (3H, s), 7.13 (1H, d, J=4.6 Hz), 7.23 (1H, dd, J=4.8-0.9 Hz), 7.32-7.37 (1H, m), 7.6 (1H, t, J=7.9 Hz), 7.73 (1H, dd, J=4.8-3.6 Hz), 7.82 (2H, d, J=9.1 Hz), 7.9 (1H, m), 7.95-7.99 (1H, m), 8.07 (1H, dd) 8.36 (2H, d, J=9.1 Hz) 8.66 (1H, s) 8.83 (1H, d, J=4.6 Hz)

MS (ES) m/z=520 (MH+)
HPLC=96.18%

Example 87

N-methyl-N-{3-[3-(thiophene-2-carbonyl)-pyrazolo[1,5-a]pyrimidin-7-yl]-phenyl}-2-thiophene-sulfonamide $^1$H NMR (400 MHz, CDCl$_3$): δ 3.35 (3H, s), 7.13-7.18 (2H, d), 7.23-7.31 (1H, m), 7.39-7.46 (2H, m), 7.58-7.68 (2H, m), 7.74-7.77 (1H, m), 7.93 (1H, d, J=1.5 Hz), 8.06 (1H, dd, J=7.9-1.2 Hz), 8.14 (1H, m), 8.72 (1H, s) 8.85 (1H, d, J=4.3 Hz)

MS (ES) m/z=481 (MH+)
HPLC=98.82%

Example 88

N-methyl-N-{3-[3-(thiophene-2-carbonyl)-pyrazolo[1,5-a]pyrimidin-7-yl]-phenyl}-5-methyl-4-isoxazolylsulfonamide $^1$H NMR (400 MHz, CDCl$_3$): δ 2.3 (3H, s), 3.29 (3H, s), 7.11 (1H, d, J=4.2 Hz), 7.21 (1H, dd, J=5.2-3.9 Hz), 7.51-7.55 (1H, m), 7.63 (1H, t, J=7.9 Hz), 7.71 (1H, dd, J=5.2-1.2 Hz), 7.91-7.94 (2H, m), 8.07 (1H, dd), 8.32 (1H, d, J=0.6 Hz) 8.7 (1H, s) 8.82 (1H, d, J=4.2 Hz)
MS (ES) m/z=480 (MH+)
HPLC=96.78%

Example 89

N-methyl-N-{3-[3-(thiophene-2-carbonyl)-pyrazolo[1,5-a]pyrimidin-7-yl]-phenyl}-2-trifluoromethyl-5-methyl-3-furylsulfonamide $^1$H NMR (400 MHz, CDCl$_3$): δ 2.23 (3H, s), 3.3 (3H, s), 7.11 (1H, d, J==4.6 Hz), 7.2-7.24 (1H, m), 7.52-7.66 (2H, m), 7.72 (1H, dd, J=4.9-1.2 Hz), 7.91-7.95 (2H, m), 8.07 (1H, dd), 8.67 (1H, s), 8.82 (1H, d, J=4.2 Hz)
MS (ES) m/z=547 (MH+)
HPLC=98.88%

Example 90

N-methyl-N-{3-[3-(thiophene-2-carbonyl)-pyrazolo[1,5-a]pyrimidin-7-yl]-phenyl}-6-(morpholin-4-yl)-3-pyridylsulfonamide $^1$H NMR (400 MHz, CDCl$_3$): δ 3.24 (3H, s), 3.62-3.67 (4H, m), 3.78-3.82 (4H, m), 6.55 (1H, d, J=9.1 Hz), 7.14 (1H, d, J=4.2 Hz), 7.21 (1H, dd, J=4.9-3.6 Hz), 7.36-7.4 (1H, m), 7.53-7.6 (2H, m), 7.72 (1H, dd, J=4.9-1.2 Hz), 7.93-8.01 (2H, m) 8.1-8.12 (1H, m) 8.39 (1H, d, J=2.4 Hz) 8.69 (1H, s) 8.81 (1H, d, J=4.6 Hz)
MS (ES) m/z=561 (MH+)
HPLC=98.7%

Example 91

N-methyl-N-{3-[(3-(thiophene-2-carbonyl)-pyrazolo[1,5-a]pyrimidin-7-yl]-phenyl}-2,4-dimethyl-5-thiazolylsulfonamide $^1$H NMR (400 MHz, CDCl$_3$): δ 2.22 (3H, s), 2.69 (3H, s), 3.35 (3H, s), 7.11 (1H, d, J=4.6 Hz), 7.2 (1H, dd), 7.43-7.47 (1H, m), 7.59 (1H, m), 7.71 (1H, dd), 7.93-7.94 (1H, m), 7.97-8.02 (1H, m) 8.09 (1H, dd, J=3.7-1.1 Hz) 8.68 (1H, s) 8.81 (1H, d, J=4.6 Hz)
MS (ES) m/z=510 (MH+)
HPLC=99.18%

Example 92

N-methyl-N-{3-[3-(thiophene-2-carbonyl)-pyrazolo[1,5-a]pyrimidin-7-yl]-phenyl}-cyclopropyl-sulfonamide $^1$H NMR (400 MHz, CDCl$_3$): δ 0.95-1.06 (2H, m), 1.09-1.18 (2H, m), 2.4-2.51 (1H, m), 3.44 (3H, s), 7.16 (1H, d, J=4.6 Hz), 7.19-7.23 (1H, m), 7.58-7.73 (3H, m), 7.96 (1H, m), 8.11 (1H, m), 8.16 (1H, m) 8.71 (1H, s) 8.82 (1H, d, J=4.2 Hz)
MS (ES) m/z=439 (MH+)
HPLC=96.7%

Example 93

N-methyl-N-{3-[3-(thiophene-2-carbonyl)-pyrazolo[1,5-a]pyrimidin-7-yl]-phenyl}-benzylsulfonamide $^1$H NMR (400 MHz, CDCl$_3$): δ 3.21 (3H, s), 4.39 (2H, s), 7.1 (1H, d, J=4.6 Hz), 7.2-7.24 (1H, m), 7.33-7.47 (6H, m), 7.54-7.6 (1H, m), 7.71 (1H, d, J=4.9 Hz), 7.87-7.92 (2H, m), 8.12 (1H, d, J=3.3 Hz), 8.74 (1H, s) 8.83 (1H, d, J=4.6 Hz)
MS (ES) m/z=489 (MH+)
HPLC=97.95%

Example 94

N-methyl-N-{3-[3-(thiophene-2-carbonyl)-pyrazolo[1,5-a]pyrimidin-7-yl]-phenyl}-vinylsulfonamide $^1$H NMR (400 MHz, CDCl$_3$): δ 3.32 (3H, s), 6.08 (1H, d, 9.7 Hz), 6.26 (1H, d, J=16.4 Hz), 6.51 (1H, dd, J=16.4-9.7 Hz), 7.15 (1H, d, J=4.2 Hz), 7.2 (1H, dd, J=4.8-3.9 Hz), 7.53-7.64 (2H, m), 7.7 (1H, dd, J=4.8-1.2 Hz), 7.94-7.98 (1H, m), 8.06-8.11 (2H, m)
MS (ES) m/z=425 (MH+)
HPLC=97.53%

Example 95

N-methyl-N-{3-[3-(thiophene-2-carbonyl)-pyrazolo[1,5-a]pyrimidin-7-yl]-phenyl}-3,5-dimethyl-4-isoxazolylsulfonamide $^1$H NMR (400 MHz, CDCl$_3$): δ 2.12 (3H, s), 2.33 (3H, s), 3.31 (3H, s), 7.1 (1H, d, 3-4.5 Hz), 7.19-7.23 (1H, m), 7.52-7.66 (2H, m), 7.71 (1H, d, J=5.5 Hz), 7.93-7.96 (2H, m), 8.07 (1H, d, J=3.6 Hz), 8.69 (1H, s) 8.82 (1H, d, J=4.2 Hz)
MS (ES) m/z=494 (MH+)
HPLC=99.17%

Example 96

N-methyl-N-{3-[3-(thiophene-2-carbonyl)-pyrazolo[1,5-a]pyrimidin-7-yl]-phenyl}-1,3,5-trimethyl-4-pyrazolylsulfonamide $^1$H NMR (400 MHz, CDCl$_3$): δ 2.09 (3H, s), 2.1 (3H, s), 3.24 (3H, s), 3.7 (3H, s), 7.1 (1H, d, J=4.2 Hz), 7.2 (1H, dd, J=4.8-3.6 Hz), 7.45-7.59 (2H, m), 7.71 (1H, dd), 7.9-7.98 (2H, m), 8.09-8.11 (1H, m), 8.67 (1H, s), 8.8 (1H, d, J=4.2 Hz)
MS (ES) m/z=507 (MH+)
HPLC=94.68%

Example 97

N-methyl-N-{3-[3-(thiophene-2-carbonyl)-pyrazolo[1,5-a]pyrimidin-7-yl]-phenyl}-propanesulfonamide $^1$H NMR (400 MHz, CDCl$_3$): δ 1.06 (3H, t, J=7.5 Hz), 1.92-1.97 (2H, m), 3.02-3.08 (2H, m), 3.43 (3H, s), 7.16 (1H, d, J=4.2 Hz), 7.19-7.23 (1H, m), 7.62-7.64 (2H, m), 7.72 (1H, m), 7.93-7.97 (1H, m), 8.11-8.14 (2H, m) 8.71 (1H, s) 8.83 (1H, d, J=4.6 Hz)

MS (ES) m/z=441 (MH+)
HPLC=97.75%

Example 98

N-methyl-N-{3-[3-(thiophene-2-carbonyl)-pyrazolo[1,5-a]pyrimidin-7-yl]-phenyl}-butanesulfonamide $^1$H NMR (400 MHz, CDCl$_3$): δ 0.93 (3H, t, J=7.5 Hz), 1.44 (2H, m), 1.77-1.89 (2H, m), 3.04-3.11 (2H, m), 3.43 (3H, s), 7.16 (1H, d, J=4.6 Hz), 7.2 (1H, dd, J=5.2-3.9 Hz), 7.61-7.64 (2H, m), 7.71 (1H, dd, J=5.2-1.2 Hz), 7.91-7.96 (1H, m) 8.1 (1H, dd, J=3.9-1.2 Hz) 8.14 (1H, m) 8.7 (1H, s) 8.82 (1H, d, J=4.3 Hz)

MS (ES) m/z=455 (MH+)
HPLC=98.54%

Example 99

N-methyl-N-{3-[3-(thiophene-2-carbonyl)-pyrazolo[1,5-a]pyrimidin-7-yl]-phenyl}-cyclopentylmethane-sulfonamide $^1$H NMR (400 MHz, CDCl$_3$): δ 1.23-1.34 (2H, m), 1.56-1.66 (4H, m), 1.95-2.03 (2H, m), 2.32-2.44 (1H, m), 3.08 (2H, d, J=7 Hz), 3.42 (3H, s), 7.16 (1H, d, J=4.2 Hz), 7.2 (1H, dd, J=4.9-3.9 Hz), 7.61-7.63 (2H, m), 7.71 (1H, dd, J=4.9-1.2 Hz) 7.91-7.96 (1H, m) 8.09-8.14 (2H, m) 8.7 (1H, s) 8.82 (1H, d, J=4.2 Hz)

MS (ES) m/z=481 (MH+)
HPLC=96.43%

Example 100

N-{3-[3-(5-methyl-[1,2,4]oxadiazol-3-yl)-pyrazolo[1,5-a]pyrimidin-7-yl]-phenyl}-methane-sulfonamide $^1$H NMR (400 MHz, CDCl$_3$); δ 2.71 (3H, s), 3.12 (3H, s), 7.08 (1H, d, J=4.4 Hz), 7.1 (1H, a), 7.43-7.46 (1H, m), 7.57 (1H, t, J=7.6 Hz), 7.80-7.83 (1H, m), 7.95 (1H, t, J=2 Hz), 8.69 (1H, s), 8.8 (1H, d, J=4.4 Hz)

MS (ES) m/z=371 (MH+)
HPLC=94%

Example 101

N-ethyl-N-{3-[3-(5-methyl-[1,2,4]oxadiazol-3-yl)-pyrazolo[1,5-a]pyrimidin-7-yl]-phenyl}-methane-sulfonamide $^1$H NMR (400 MHz, CDCl$_3$): δ 1.21 (3H, t, J=7.2 Hz), 2.69 (3H, s), 2.95 (3H, s), 3.81 (2H, q, J=7.2 Hz), 7.1 (1H, d, J=4.8 Hz), 7.56-7.58 (1H, m), 7.64 (1H, t, J=8 Hz), 8.04 (1H, d, J=8 Hz), 8.09 (1H, t, J=2 Hz), 8.69 (1H, s), 8.817 (1H, d, J=4.8 Hz)

MS (ES) m/z=399 (MH$^+$)
HPLC=94%

Example 102

5 mg tablets

| | |
|---|---|
| Compound of Example 2 | 5.0 mg |
| Colloidal silicon dioxide | 0.6 mg |
| Croscarmellose sodium | 12.0 mg |
| Talc | 4.0 mg |
| Magnesium stearate | 1.5 mg |
| Polysorbate 80 | 1.0 mg |
| Lactose | 75.0 mg |
| Hydroxypropyl methylcellulose | 3.0 mg |
| Polyethylene glycol 4000 | 0.5 mg |
| Titanium dioxide E171 | 1.5 mg |
| Microcrystalline cellulose q.s. to | 125.0 mg |

Example 103

10 mg Capsules

| | |
|---|---|
| Compound of Example 2 | 10.0 mg |
| Colloidal silicon dioxide | 0.6 mg |
| Crospovidone | 12.0 mg |
| Talc | 4.0 mg |
| Magnesium stearate | 1.5 mg |
| Lauryl sulfate sodium | 1.5 mg |
| Lactose | 77.0 mg |
| Gelatin | 28.5 mg |
| Titanium dioxide E171 | 1.5 mg |
| Indigotin E132 | 0.02 mg |
| Microcrystalline cellulose q.s. to | 155.0 mg |

Example 104

Oral Drops

| | |
|---|---|
| Compound of Example 2 | 0.5 g |
| Propylene glycol | 10.0 g |
| Glycerin | 5.0 g |
| Saccharin sodium | 0.1 g |
| Polysorbate 80 | 1.0 g |
| Lemon flavor | 0.2 g |
| Ethanol | 25.0 mL |
| Purified water q.s. to | 100.0 mL |

Example 105

2.5 mg Tablets

| | |
|---|---|
| Compound of Example 16 | 2.5 mg |
| Colloidal silicon dioxide | 0.6 mg |
| Croscarmellose sodium | 12.0 mg |
| Talc | 4.0 mg |
| Magnesium stearate | 1.5 mg |
| Polysorbate 80 | 1.0 mg |
| Lactose | 75.0 mg |

-continued

| | |
|---|---|
| Hydroxypropyl methylcellulose | 3.0 mg |
| Polyethylene glycol 4000 | 0.5 mg |
| Titanium dioxide E171 | 1.5 mg |
| Microcrystalline cellulose q.s. tp | 125.0 mg |

Example 106

5 mg Capsules

| | |
|---|---|
| Compound of Example 16 | 5.0 mg |
| Colloidal silicon dioxide | 0.6 mg |
| Crospovidone | 12.0 mg |
| Talc | 4.0 mg |
| Magnesium stearate | 1.5 mg |
| Lauryl sulfate sodium | 1.5 mg |
| Lactose | 77.0 mg |
| Gelatin | 28.5 mg |
| Titanium dioxide E171 | 1.5 mg |
| Indigotin E132 | 0.02 mg |
| Microcrystalline q.s. to | 155.0 mg |

Example 107

Oral Drops

| | |
|---|---|
| Compound of Example 16 | 0.25 g |
| Propylene glycol | 10.0 g |
| Glycerin | 5.0 g |
| Saccharin sodium | 0.1 g |
| Polysorbate 80 | 1.0 g |
| Lemon flavor | 0.2 g |
| Ethanol | 25.0 mL |
| Purified q.s. to | 100.0 mL |

The invention claimed is:
1. A compound of formula (I):

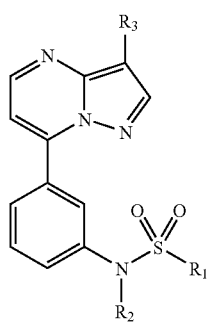

(I)

as well as pharmaceutically acceptable salts thereof; wherein R$_1$ is selected from the group consisting of alkyl(C$_1$-C$_6$), alkenyl(C$_2$-C$_6$), ω,ω,ω-trifluoroalkyl(C$_1$-C$_6$), cycloalkyl(C$_3$-C$_6$), cycloalkyl(C$_3$-C$_6$)alkyl(C$_1$-C$_6$), phenyl, monosubstituted phenyl, disubstituted phenyl, phenylalkyl(C$_1$-C$_6$), phenylalkenyl(C$_2$-C$_6$), furyl, substituted furyl, isoxazolyl, substituted isoxazolyl, pyrazolyl, substituted pyrazolyl, thienyl, substituted thienyl, thiazolyl, substituted thiazolyl, pyridyl and substituted pyridyl;

R$_2$ is selected from the group consisting of hydrogen, alkyl (C$_1$-C$_6$), alkenyl(C$_2$-C$_6$), alkynyl(C$_2$-C$_6$) and cycloalkyl (C$_3$-C$_6$);

R$_3$ is selected from the group consisting of —CN and —COR$_6$ wherein R$_6$ is selected from the group consisting of hydrogen, alkyl(C$_1$-C$_6$), alkenyl(C$_2$-C$_6$), alkynyl (C$_2$-C$_6$), cycloalkyl(C$_3$-C$_6$), phenyl, monosubstituted phenyl, disubstituted phenyl, phenylalkyl(C$_1$-C$_6$), phenylalkenyl(C$_2$-C$_6$), furyl, substituted furyl, thienyl, substituted thienyl, thiazolyl, substituted thiazolyl, oxadiazolyl, substituted oxadiazolyl, pyridyl and substituted pyridyl;

with the proviso that simultaneously: R$_1$ may not be p-tolyl and R$_2$ methyl and R$_3$ benzoyl; and R$_1$ may not be p-tolyl and R$_2$ ethyl and R$_3$ furyl-2-carbonyl.

2. A compound according to claim 1, wherein R$_1$ and R$_2$ are independently as defined in formula (I) and R$_3$ is a cyano group.

3. A compound according to claim 2, wherein R$_1$ is selected from the group consisting of methyl, ethyl, n-propyl, i-propyl, n-butyl, phenyl and 4-methoxyphenyl; and R$_2$ is selected from the group consisting of methyl, ethyl, n-propyl, i-propyl, n-butyl, cyclopropyl and 2-propynyl.

4. A compound according to claim 1, wherein R$_1$ and R$_2$ are independently as defined in formula (I) and R$_3$ is a thiophene-2-carbonyl group.

5. A compound according to claim 4, wherein R$_1$ is selected from the group consisting of methyl, ethyl, n-propyl, i-propyl, n-butyl, 2-phenylethenyl, 2,2,2-trifluoroethyl, phenyl, 2-chlorophenyl, 3-chlorophenyl, 4-chlorophenyl, 2,4-dichlorophenyl, 3,4-dichlorophenyl, 2-cyanophenyl, 3-cyanophenyl, 4-cyanophenyl, 4-methoxyphenyl, 3-nitrophenyl, 4-nitrophenyl, 2-thienyl, 5-methyl-4-isoxazolyl, 5-methyl-2-trifluoromethyl-3-furyl, 4-(4-morpholinyl)-3-pyridyl, 2,4-dimethyl-5-thiazolyl, cyclopropyl, benzyl, vinyl, 3,5-dimethyl-4-isoxazolyl, 1,3,5-trimethyl-4-pyrazolyl and cyclopentylmethyl; and R$_2$ is selected from the group consisting of hydrogen, methyl, ethyl, n-propyl, i-propyl, n-butyl, cyclopropyl and 2-propynyl.

6. A compound according to claim 1, wherein R$_1$ and R$_2$ are independently as defined in formula (I) and R$_3$ is a benzoyl group.

7. A compound according to claim 6 wherein R$_1$ is selected from the group consisting of methyl and ethyl; and R$_2$ is selected from the group consisting of methyl, ethyl and 2-propynyl.

8. A compound according to claim 1, wherein R$_1$ and R$_2$ are independently as defined in formula (I) and R$_3$ is a 4-fluorobenzoyl group.

9. A compound according to claim 8 wherein R$_1$ is selected from the group consisting of methyl and ethyl; and R$_2$ is selected from the group consisting of methyl, ethyl and 2-propynyl.

10. A compound according to claim 1, wherein R$_1$ and R$_2$ are independently as defined in formula (I) and R$_3$ is a 4-methylbenzoyl group.

11. A compound according to claim 10 wherein R$_1$ is selected from the group consisting of methyl and ethyl; and R$_2$ is selected from the group consisting of methyl, ethyl and 2-propynyl.

12. A compound according to claim 1, wherein R$_1$ and R$_2$ are independently as defined in formula (I) and R$_3$ is a 4-methoxybenzoyl group.

13. A compound according to claim 12 wherein R$_1$ is selected from the group consisting of methyl and ethyl; and R$_2$ is selected from the group consisting of methyl, ethyl and 2-propynyl.

14. A compound according to claim 1, wherein $R_1$ and $R_2$ are independently as defined in formula (I) and $R_3$ is a pyridyl-2-carbonyl group.

15. A compound according to claim 14 wherein $R_1$ is selected from the group consisting of methyl and ethyl; and $R_2$ is selected from the group consisting of methyl, ethyl and 2-propynyl.

16. A compound according to claim 1, wherein $R_1$ and $R_2$ are independently as defined in formula (I) and $R_3$ is a pyridyl-4-carbonyl group.

17. A compound according to claim 16 wherein $R_1$ is selected from the group consisting of methyl and ethyl; and $R_2$ is selected from the group consisting of methyl, ethyl and 2-propynyl.

18. A compound according to claim 2 or claim 3, wherein said compound is selected from the group consisting of:
- N-[3-(3-cyano-pyrazolo[1,5-a]pyrimidin-7-yl)-phenyl]-N-methyl-methanesulfonamide;
- N-[3-(3-cyano-pyrazolo[1,5-a]pyrimidin-7-yl)-phenyl]-N-ethyl-methanesulfonamide;
- N-[3-(3-cyano-pyrazolo[1,5-a]pyrimidin-7-yl)-phenyl]-N-methyl-benzenesulfonamide;
- N-[3-(3-cyano-pyrazolo[1,5-a]pyrimidin-7-yl)-phenyl]-N-ethyl-benzenesulfonamide;
- N-[3-(3-cyano-pyrazolo[1,5-a]pyrimidin-7-yl)-phenyl]-N-prop-2-ynyl-methanesulfonamide;
- N-[3-(3-cyano-pyrazolo[1,5-a]pyrimidin-7-yl)-phenyl]-N-propyl-ethanesulfonamide;
- N-[3-(3-cyano-pyrazolo[1,5-a]pyrimidin-7-yl)-phenyl]-N-ethyl-ethanesulfonamide;
- N-[3-(3-cyano-pyrazolo[1,5-a]pyrimidin-7-yl)-phenyl]-N-prop-2-ynyl-propane-2-sulfonamide;
- N-[3-(3-cyano-pyrazolo[1,5-a]pyrimidin-7-yl)-phenyl]-N-methyl-ethanesulfonamide;
- N-[3-(3-cyano-pyrazolo[1,5-a]pyrimidin-7-yl)-phenyl]-N-butyl-ethanesulfonamide;
- N-[3-(3-cyano-pyrazolo[1,5-a]pyrimidin-7-yl)-phenyl]-N-methyl-2-propanesulfonamide;
- N-[3-(3-cyano-pyrazolo[1,5-a]pyrimidin-7-yl)-phenyl]-N-ethyl-2-propanesulfonamide;
- N-[3-(3-cyano-pyrazolo[1,5-a]pyrimidin-7-yl)-phenyl]-N-butyl-2-propanesulfonamide;
- N-[3-(3-cyano-pyrazolo[1,5-a]pyrimidin-7-yl)-phenyl]-N-propyl-2-propanesulfonamide; and
- N-[3-(3-cyano-pyrazolo[1,5-a]pyrimidin-7-yl)-phenyl]-N-prop-2-ynyl-ethanesulfonamide.

19. A compound according to claim 4 or claim 5, wherein said compound is selected from the group consisting of:
- N-methyl-N-{3-[3-(thiophene-2-carbonyl)-pyrazolo[1,5-a]pyrimidin-7-yl]-phenyl}-methanesulfonamide;
- N-ethyl-N-{3-[3-(thiophene-2-carbonyl)-pyrazolo[1,5-a]pyrimidin-7-yl]-phenyl}-methanesulfonamide;
- N-methyl-N-{3-[3-(thiophene-2-carbonyl)-pyrazolo[1,5-a]pyrimidin-7-yl]-phenyl}-benzenesulfonamide;
- N-ethyl-N-{3-[3-(thiophene-2-carbonyl)-pyrazolo[1,5-a]pyrimidin-7-yl]-phenyl}-benzenesulfonamide;
- N-prop-2-ynyl-N-{3-[3-(thiophene-2-carbonyl)-pyrazolo[1,5-a]pyrimidin-7-yl]-phenyl}-methanesulfonamide;
- N-propyl-N-{3-[3-(thiophene-2-carbonyl)-pyrazolo[1,5-a]pyrimidin-7-yl]-phenyl}-ethanesulfonamide;
- N-ethyl-N-{3-[3-(thiophene-2-carbonyl)-pyrazolo[1,5-a]pyrimidin-7-yl]-phenyl}-ethanesulfonamide;
- N-prop-2-ynyl-N-{3-[3-(thiophene-2-carbonyl)-pyrazolo[1,5-a]pyrimidin-7-yl]-phenyl}-2-propanesulfonamide;
- N-methyl-N-{3-[3-(thiophene-2-carbonyl)-pyrazolo[1,5-a]pyrimidin-7-yl]-phenyl}-ethanesulfonamide;
- N-butyl-N-{3-[3-(thiophene-2-carbonyl)-pyrazolo[1,5-a]pyrimidin-7-yl]-phenyl}-ethanesulfonamide;
- N-methyl-N-{3-[3-(thiophene-2-carbonyl)-pyrazolo[1,5-a]pyrimidin-7-yl]-phenyl}-2-propanesulfonamide;
- N-ethyl-N-{3-[3-(thiophene-2-carbonyl)-pyrazolo[1,5-a]pyrimidin-7-yl]-phenyl}-2-propanesulfonamide;
- N-propyl-N-{3-[3-(thiophene-2-carbonyl)-pyrazolo[1,5-a]pyrimidin-7-yl]-phenyl}-2-propanesulfonamide;
- N-butyl-N-{3-[3-(thiophene-2-carbonyl)-pyrazolo[1,5-a]pyrimidin-7-yl]-phenyl}-2-propanesulfonamide;
- N-methyl-N-{3-[3-(thiophene-2-carbonyl)-pyrazolo[1,5-a]pyrimidin-7-yl]-phenyl}-2-phenylethenesulfonamide;
- N-methyl-N-{3-[3-(thiophene-2-carbonyl)-pyrazolo[1,5-a]pyrimidin-7-yl]-phenyl}-2,2,2-trifluoroethanesulfonamide;
- N-methyl-N-{3-[3-(thiophene-2-carbonyl)-pyrazolo[1,5-a]pyrimidin-7-yl]-phenyl}-2-chlorobenzenesulfonamide;
- N-methyl-N-{3-[3-(thiophene-2-carbonyl)-pyrazolo[1,5-a]pyrimidin-7-yl]-phenyl}-3-chlorobenzenesulfonamide;
- N-methyl-N-{3-[3-(thiophene-2-carbonyl)-pyrazolo[1,5-a]pyrimidin-7-yl]-phenyl}-4-chlorobenzenesulfonamide;
- N-methyl-N-{3-[3-(thiophene-2-carbonyl)-pyrazolo[1,5-a]pyrimidin-7-yl]-phenyl}-2,4-dichlorobenzenesulfonamide;
- N-methyl-N-{3-[3-(thiophene-2-carbonyl)-pyrazolo[1,5-a]pyrimidin-7-yl]-phenyl}-3,4-dichlorobenzenesulfonamide;
- N-methyl-N-{3-[3-(thiophene-2-carbonyl)-pyrazolo[1,5-a]pyrimidin-7-yl]-phenyl}-2-cyano-benzenesulfonamide;
- N-methyl-N-{3-[3-(thiophene-2-carbonyl)-pyrazolo[1,5-a]pyrimidin-7-yl]-phenyl}-3-cyano-benzenesulfonamide;
- N-methyl-N-{3-[3-(thiophene-2-carbonyl)-pyrazolo[1,5-a]pyrimidin-7-yl]-phenyl}-4-cyano-benzenesulfonamide;
- N-methyl-N-{3-[3-(thiophene-2-carbonyl)-pyrazolo[1,5-a]pyrimidin-7-yl]-phenyl}-3-nitro-benzenesulfonamide;
- N-methyl-N-{3-[3-(thiophene-2-carbonyl)-pyrazolo[1,5-a]pyrimidin-7-yl]-phenyl}-4-nitro-benzenesulfonamide;
- N-methyl-N-{3-[3-(thiophene-2-carbonyl)-pyrazolo[1,5-a]pyrimidin-7-yl]-phenyl}-2-thiophenesulfonamide;
- N-methyl-N-{3-[3-(thiophene-2-carbonyl)-pyrazolo[1,5-a]pyrimidin-7-yl]-phenyl}-5-methyl-4-isoxazolyl-sulfonamide;
- N-methyl-N-{3-[3-(thiophene-2-carbonyl)-pyrazolo[1,5-a]pyrimidin-7-yl]-phenyl}-2-trifluoromethyl-5-methyl-3-furyl-sulfonamide;
- N-methyl-N-{3-[3-(thiophene-2-carbonyl)-pyrazolo[1,5-a]pyrimidin-7-yl]-phenyl}-6-(morpholin-4-yl)-3-pyridyl-sulfonamide;
- N-methyl-N-{3-[3-(thiophene-2-carbonyl)-pyrazolo[1,5-a]pyrimidin-7-yl]-phenyl}-2,4-dimethyl-5-thiazolyl-sulfonamide;
- N-methyl-N-{3-[3-(thiophene-2-carbonyl)-pyrazolo[1,5-a]pyrimidin-7-yl]-phenyl}-cyclopropylsulfonamide;
- N-methyl-N-{3-[3-(thiophene-2-carbonyl)-pyrazolo[1,5-a]pyrimidin-7-yl]-phenyl}-benzylsulfonamide;
- N-methyl-N-{3-[3-(thiophene-2-carbonyl)-pyrazolo[1,5-a]pyrimidin-7-yl]-phenyl}-vinylsulfonamide;

N-methyl-N-{3-[3-(thiophene-2-carbonyl)-pyrazolo[1,5-a]pyrimidin-7-yl]-phenyl}-3,5-dimethyl-4-isoxazolyl-sulfonamide;
N-methyl-N-{3-[3-(thiophene-2-carbonyl)-pyrazolo[1,5-a]pyrimidin-7-yl]-phenyl}-1,3,5-trimethyl-4-pyrazolyl-sulfonamide;
N-methyl-N-{3-[3-(thiophene-2-carbonyl)-pyrazolo[1,5-a]pyrimidin-7-yl]-phenyl}-propanesulfonamide;
N-methyl-N-{3-[3-(thiophene-2-carbonyl)-pyrazolo[1,5-a]pyrimidin-7-yl]-phenyl}-butanesulfonamide; and
N-methyl-N-{3-[3-(thiophene-2-carbonyl)-pyrazolo[1,5-a]pyrimidin-7-yl]-phenyl}-cyclopentylmethane-sulfonamide.

20. A compound according to claim 6 or claim 7 wherein said compound is selected from the group consisting of:
N-methyl-N-{3-[3-(benzoyl)-pyrazolo[1,5-a]pyrimidin-7-yl]-phenyl}-methane sulfonamide;
N-ethyl-N-{3-[3-(benzoyl)-pyrazolo[1,5-a]pyrimidin-7-yl]-phenyl}-methanesulfonamide;
N-methyl-N-{3-[3-(benzoyl)-pyrazolo[1,5-a]pyrimidin-7-yl]-phenyl}-ethanesulfonamide;
N-ethyl-N-{3-[3-(benzoyl)-pyrazolo[1,5-a]pyrimidin-7-yl]-phenyl}-ethane sulfonamide;
N-prop-2-ynyl-N-{3-[3-(benzoyl)-pyrazolo[1,5-a]pyrimidin-7-yl]-phenyl}-ethanesulfonamide; and
N-prop-2-ynyl-N-{3-[3-(benzoyl)-pyrazolo[1,5-a]pyrimidin-7-yl]-phenyl}-methanesulfonamide.

21. A compound according to claim 8 or claim 9 wherein said compound is selected from the group consisting of:
N-methyl-N-{3-[3-(fluorobenzene-4-carbonyl)-pyrazolo[1,5-a]pyrimidin-7-yl]-phenyl}-methanesulfonamide;
N-ethyl-N-{3-[3-(fluorobenzene-4-carbonyl)-pyrazolo[1,5-a]pyrimidin-7-yl]-phenyl}-methanesulfonamide;
N-methyl-N-{3-[3-(fluorobenzene-4-carbonyl)-pyrazolo[1,5-a]pyrimidin-7-yl]-phenyl}-ethanesulfonamide;
N-ethyl-N-{3-[3-(fluorobenzene-4-carbonyl)-pyrazolo[1,5-a]pyrimidin-7-yl]-phenyl}-ethanesulfonamide;
N-prop-2-ynyl-N-{3-[3-(fluorobenzene-4-carbonyl)-pyrazolo[1,5-a]pyrimidin-7-yl]-phenyl}-ethanesulfonamide; and
N-prop-2-ynyl-N-{3-[3-(fluorobenzene-4-carbonyl)-pyrazolo[1,5-a]pyrimidin-7-yl]-phenyl}-methanesulfonamide.

22. A compound according to claim 10 or claim 11 wherein said compound is selected from the group consisting of:
N-methyl-N-{3-[3-(4-methylbenzoyl)-pyrazolo[1,5-a]pyrimidin-7-yl]-phenyl}-methanesulfonamide;
N-ethyl-N-{3-[3-(4-methylbenzoyl)-pyrazolo[1,5-a]pyrimidin-7-yl]-phenyl}-methanesulfonamide;
N-methyl-N-{3-[3-(4-methylbenzoyl)-pyrazolo[1,5-a]pyrimidin-7-yl]-phenyl}-ethanesulfonamide;
N-ethyl-N-{3-[3-(4-methylbenzoyl)-pyrazolo[1,5-a]pyrimidin-7-yl]-phenyl}-ethanesulfonamide;
N-prop-2-ynyl-N-{3-[3-(4-methylbenzoyl)-pyrazolo[1,5-a]pyrimidin-7-yl]-phenyl}-ethanesulfonamide; and
N-prop-2-ynyl-N-{3-[3-(4-methylbenzoyl)-pyrazolo[1,5-a]pyrimidin-7-yl]-phenyl}-methanesulfonamide.

23. A compound according to claim 12 or claim 13 wherein said compound is selected from the group consisting of:
N-methyl-N-{3-[3-(4-methoxybenzoyl)-pyrazolo[1,5-a]pyrimidin-7-yl]-phenyl}-methanesulfonamide;
N-ethyl-N-{3-[3-(4-methoxybenzoyl)-pyrazolo[1,5-a]pyrimidin-7-yl]-phenyl}-methanesulfonamide;
N-methyl-N-{3-[3-(4-methoxybenzoyl)-pyrazolo[1,5-a]pyrimidin-7-yl]-phenyl}-ethanesulfonamide;
N-ethyl-N-{3-[3-(4-methoxybenzoyl)-pyrazolo[1,5-a]pyrimidin-7-yl]-phenyl}-ethanesulfonamide;
N-prop-2-ynyl-N-{3-[3-(4-methoxybenzoyl)-pyrazolo[1,5-a]pyrimidin-7-yl]-phenyl}-ethanesulfonamide; and
N-prop-2-ynyl-N-{3-[3-(4-methoxybenzoyl)-pyrazolo[1,5-a]pyrimidin-7-yl]-phenyl}-methanesulfonamide.

24. A compound according to claim 14 or claim 15 wherein said compound is selected from the group consisting of:
N-methyl-N-{3-[3-(pyridin-2-carbonyl)-pyrazolo[1,5-a]pyrimidin-7-yl]-phenyl}-methanesulfonamide;
N-ethyl-N-{3-[3-(pyridin-2-carbonyl)-pyrazolo[1,5-a]pyrimidin-7-yl]-phenyl}-methanesulfonamide;
N-prop-2-ynyl-N-{3-[3-(pyridin-2-carbonyl)-pyrazolo[1,5-a]pyrimidin-7-yl]-phenyl}-methanesulfonamide;
N-methyl-N-{3-[3-(pyridin-2-carbonyl)-pyrazolo[1,5-a]pyrimidin-7-yl]-phenyl}-ethanesulfonamide;
N-ethyl-N-{3-[3-(pyridin-2-carbonyl)-pyrazolo[1,5-a]pyrimidin-7-yl]-phenyl}-ethanesulfonamide; and
N-prop-2-ynyl-N-{3-[3-(pyridin-2-carbonyl)-pyrazolo[1,5-a]pyrimidin-7-yl]-phenyl}-ethanesulfonamide.

25. A compound according to claim 16 or claim 17 wherein said compound is selected from the group consisting of:
N-methyl-N-{3-[3-(pyridin-4-carbonyl)-pyrazolo[1,5-a]pyrimidin-7-yl]-phenyl}-methanesulfonamide;
N-ethyl-N-{3-[3-(pyridin-4-carbonyl)-pyrazolo[1,5-a]pyrimidin-7-yl]-phenyl}-methanesulfonamide;
N-methyl-N-{3-[3-(pyridin-4-carbonyl)-pyrazolo[1,5-a]pyrimidin-7-yl]-phenyl}-ethanesulfonamide;
N-ethyl-N-{3-[3-(pyridin-4-carbonyl)-pyrazolo[1,5-a]pyrimidin-7-yl]-phenyl}-ethanesulfonamide;
N-prop-2-ynyl-N-{3-[3-(pyridin-4-carbonyl)-pyrazolo[1,5-a]pyrimidin-7-yl]-phenyl}-ethanesulfonamide; and
N-prop-2-ynyl-N-{3-[3-(pyridin-4-carbonyl)-pyrazolo[1,5-a]pyrimidin-7-yl]-phenyl}-methanesulfonamide.

26. A process for preparing a compound of formula (I) or a pharmaceutically acceptable salt thereof, according to claim 1, comprising reacting intermediate (II):

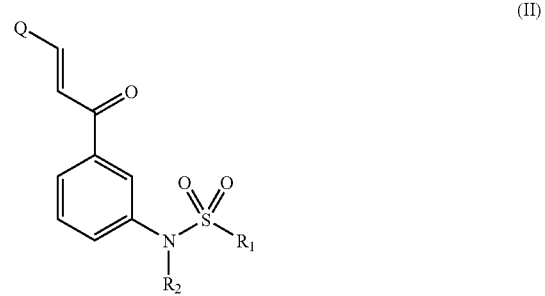

(II)

wherein $R_1$ and $R_2$ are as defined in (I) and Q is an appropriate leaving group selected from the group consisting of N(dialkyl($C_1$-$C_6$)), alkylthio($C_1$-$C_6$) and alkoxy($C_1$-$C_6$), with intermediate (III):

(III)

wherein R₃ is as defined in (I) and alternatively, treatment of the compounds of claim 1, in the form of free base, with an acid to form a salt thereof.

27. A process according to claim 26, comprising utilizing the intermediate of formula (II) where Q is selected from the group consisting of dimethylamino, methylthio and methoxy.

28. A method for treating anxiety in a mammal which comprises administering to said mammal an effective amount of a compound of claim 1 or a pharmaceutically acceptable salt thereof.

29. A method for treating epilepsy in a mammal which comprises administering to said mammal an effective amount of a compound of claim 1 or a pharmaceutically acceptable salt thereof.

30. A method for treating insomnia in a mammal which comprises administering to said mammal an effective amount of a compound of claim 1 or a pharmaceutically acceptable salt thereof.

31. A method for inducing muscle relaxation in a mammal which comprises administering to said mammal an effective amount of a compound of claim 1 or a pharmaceutically acceptable salt thereof.

32. A composition comprising a therapeutically effective amount of a compound of claim 1 or a pharmaceutically acceptable salt thereof and a therapeutically inert carrier.

* * * * *